US008563657B2

(12) United States Patent
Hsiao et al.

(10) Patent No.: US 8,563,657 B2
(45) Date of Patent: Oct. 22, 2013

(54) IONIC LIQUIDS, FUNCTIONALIZED PARTICULATES, AND FLUOROPOLYMER COMPOSITES

(75) Inventors: Benjamin S. Hsiao, Setauket, NY (US); Benjamin Chu, Setauket, NY (US); Jie Wei, Port Jefferson Station, NY (US); Hongyang Ma, Setauket, NY (US); Feng Zuo, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 231 days.

(21) Appl. No.: 12/936,330

(22) PCT Filed: Apr. 6, 2009

(86) PCT No.: PCT/US2009/039585
§ 371 (c)(1),
(2), (4) Date: Oct. 4, 2010

(87) PCT Pub. No.: WO2009/146146
PCT Pub. Date: Dec. 3, 2009

(65) Prior Publication Data
US 2011/0033647 A1    Feb. 10, 2011

Related U.S. Application Data

(60) Provisional application No. 61/042,438, filed on Apr. 4, 2008.

(51) Int. Cl.
*C08F 271/02* (2006.01)
*C08F 8/32* (2006.01)
*C08C 19/22* (2006.01)

(52) U.S. Cl.
USPC ........ 525/281; 525/279; 525/244; 525/326.2; 525/326.3; 525/374; 525/375; 977/778; 977/783; 977/734; 977/742; 977/745; 977/746; 977/748

(58) Field of Classification Search
USPC ........... 525/279, 281, 244, 326.2, 326.3, 374, 525/375; 977/778, 783, 734, 742, 745, 746, 977/748
See application file for complete search history.

(56) References Cited

U.S. PATENT DOCUMENTS

| | | | |
|---|---|---|---|
| 6,334,926 B1 * | 1/2002 | Kang et al. | 156/272.6 |
| 2004/0189762 A1 | 9/2004 | Chen | |
| 2010/0160503 A1 * | 6/2010 | Nakagawa et al. | 524/105 |

FOREIGN PATENT DOCUMENTS

WO    WO 2006/137475    * 12/2006

OTHER PUBLICATIONS

Merrigan, Chem. Commun., 2000, 2051-2052.*
Xue et al., Ionic liquids with fluorine-containing cations, European Journal of Inorganic Chemistry, Jul. 2005, vol. 2005, pp. 2573-2580.

(Continued)

*Primary Examiner* — Robert C Boyle
(74) *Attorney, Agent, or Firm* — Scully, Scott, Murphy & Presser, P.C.

(57) ABSTRACT

The present invention relates to (i) novel fluoroionic compounds capable of dispersing particulate filler compositions into a fluoropolymer; (ii) novel particulate compositions in which particulates are surface-functionalized with a fluoroionic compound; (iii) fluoropolymer composite materials containing the surface-functionalized particulates of (ii) incorporated into a fluoropolymer; (iv) crosslinked versions of (iii); v) methods for producing the crosslinked material of (iv); and (vi) articles of manufacture containing the compositions (iii) and (iv).

28 Claims, 10 Drawing Sheets

(56) References Cited

OTHER PUBLICATIONS

Lee, Functionalized imidazolium salts for task-specific ionic liquids and their applications, Chemical Communications, Mar. 14, 2006, Issue 10, pp. 1049-1063.

Chun, Palladium nanoparticles supported onto ionic carbon nanotubes as robust recyclable catalysts in an ionic liquid, Chemical Communications, Feb. 28, 2008, Issue 8, pp. 942-944.

Chen et al., In-Situ X-ray Deformation Study of Fluorinated Multiwalled Carbon Nanotube and Fluorinated Ethylene Propylene Nanocomposite Fibers, Macromolecules, Aug. 8, 2006, vol. 39, pp. 5427-5437.

International Search Report mailed Dec. 28, 2009 from the Korean Intellectual Property Office in corresponding International Application No. PCT/US2009/039585.

* cited by examiner

IONIC LIQUIDS, FUNCTIONALIZED PARTICULATES, AND FLUOROPOLYMER COMPOSITES

CROSS-REFERENCE TO RELATED APPLICATIONS

This application claims the benefit of U.S. Provisional Application No. 61/042,438 filed on Apr. 4, 2008.

STATEMENT REGARDING FEDERALLY SPONSORED RESEARCH

This invention was made with government support under grant number DMR0454887 awarded by the National Science Foundation. The government has certain rights in the invention.

FIELD OF THE INVENTION

The present invention relates to novel ionic liquids, functionalized particulates, and fluoropolymer composites incorporating the functionalized particulates.

BACKGROUND OF THE INVENTION

Fluoropolymer materials are used in printing rollers (e.g., paper feed rollers) commonly used in photocopying machines and printers. The preference for fluoropolymer materials for this purpose is primarily due to the known chemical inertness, elasticity, and low surface tension of this class of polymers. In particular, their low surface tension endows them with the necessary property of being non-sticking (i.e., releasing) when feeding or directing paper.

However, fluoropolymer materials typically suffer from numerous serious drawbacks. First, the required elasticity diminishes over time with use. This process, also known as creeping, eventually renders a printing roller unusable. This vulnerability of the printing roller is very often the first occurrence of malfunction of a photocopier. Since replacing a printing roller can be troublesome and expensive, it is not unusual that a photocopier with this problem is discarded in favor of a new photocopier. The time and effort directed to repairing a malfunctioning photocopier, or the cost of purchasing a new one, pose serious inconveniences to the consumer.

At least one of the causes believed to contribute to loss of elasticity of fluoropolymer materials is the low thermal conductivity typical for this class of polymers. The low thermal conductivity causes the fluoropolymer materials to operate at higher temperatures. This quickens the loss of elasticity, which in turn severely shortens its useful lifetime.

Though it is generally known in the art to incorporate filler material into polymers to alter their properties, this practice is severely hampered in the case of fluoropolymers due to the incompatibility of fluoropolymers with most other materials, particularly filler materials. Because of this incompatibility, filler materials typically agglomerate and remain predominantly non-dispersed in a fluoropolymer matrix. This agglomeration severely restricts the efficacy of the filler in a fluoropolymer matrix.

Accordingly, there remains a need in the art for improving the properties and increasing the usable lifetime of fluoropolymer materials while retaining their elastic and low surface tension properties.

SUMMARY OF THE INVENTION

These and other objectives, as will be apparent to those having ordinary skill in the art, have been achieved by providing (i) novel fluoroionic compounds capable of dispersing particulate filler compositions into a fluoropolymer; (ii) novel particulate compositions in which particulates are surface-functionalized with a fluoroionic compound; (iii) fluoropolymer composite materials containing the surface-functionalized particulates of (ii) incorporated into a fluoropolymer; (iv) crosslinked versions of (iii); v) methods for achieving the crosslinked material of (iv); and (vi) articles of manufacture from (iii) and (iv).

In a first aspect, the invention is directed to fluoroionic compounds of the formula

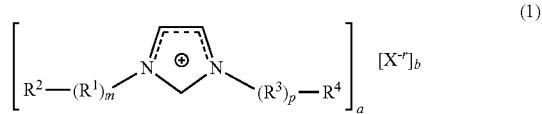

wherein $R^1$ and $R^3$ are, independently, hydrocarbon linking groups having at least one carbon atom, and optionally including one or more non-fluoro heteroatoms or heteroatom-containing groups; $R^2$ is either a hydrogen atom, or a fluoro-substituted hydrocarbon group having at least one carbon atom and at least one fluorine atom and optionally including one or more non-fluoro heteroatoms or heteroatom-containing groups, or a heteroatom-containing group only when m is 1; $R^4$ is a fluoro-substituted hydrocarbon group having at least one carbon atom and at least one fluorine atom and optionally including one or more non-fluoro heteroatoms or heteroatom-containing groups; the subscripts m and p are independently 0 or 1, where a value of 0 for a subscript represents the absence of a group to which the subscript is appended, and a value of 1 represents the presence of a group to which the subscript is appended; $X^{-r}$ represents an anion with negative charge $-r$, where r is a value of 1, 2, or 3; and the subscripts a and b are positive integers such that $a = b \times r$.

In a second aspect, the invention is directed to a surface-functionalized particulate composition containing a particulate having adhered to its surface an ionic compound of the general formula

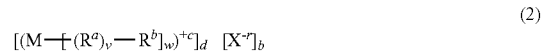

wherein M represents a ring or ring system containing at least one nitrogen atom in the ring or ring system; $R^a$ is a hydrocarbon linking group bound to a nitrogen atom of M and having at least one carbon atom, and optionally including one or more non-fluoro heteroatoms or heteroatom-containing groups; $R^b$ is a fluoro-substituted hydrocarbon group having at least one carbon atom and at least one fluorine atom and optionally including one or more non-fluoro heteroatoms or heteroatom-containing groups; the subscript v is 0 or 1, where a value of 0 for a subscript represents the absence of a group to which the subscript is appended, and a value of 1 represents the presence of a group to which the subscript is appended; the subscript w is a positive integer representing the number of $-(R^a)_v-R^b$ units bound to an equal number of ring nitrogen atoms; $+c$ represents a positive charge of magnitude c having a value of at least 1 and equal to the number of ring nitrogen atoms bound to $-(R^a)_v-R^b$ units; $X^{-r}$ represents an anion with negative charge $-r$, where r is a value of 1, 2, or 3; and the subscripts b and d are integers such that $c \times d = b \times r$.

In more specific embodiments, the particulate has adhered to its surface a fluoroionic compound according to formula (1) above, or a fluoroionic compound of the general formula

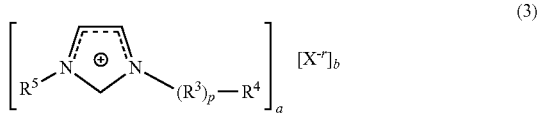

(3)

wherein $R^3$ is a hydrocarbon linking group having 1 to 6 carbon atoms; $R^4$ is a fluoro-substituted hydrocarbon group having 1 to 30 carbon atoms and at least one fluorine atom; $R^5$ is a hydrocarbon group having 1 to 6 carbon atoms; the subscript p is 0 or 1, where a value of 0 for a subscript represents the absence of a group to which the subscript is appended, and a value of 1 represents the presence of a group to which the subscript is appended; $X^{-r}$ represents an anion with negative charge −r, where r is a value of 1, 2, or 3; and the subscripts a and h are positive integers such that a=b×r.

In a third aspect, the invention is directed to fluoropolymer composite materials that contain the above-described particulate compositions incorporated into a fluoropolymer. In a particular embodiment, the fluoropolymer composite material includes crosslinking, i.e., by the presence of crosslinked bonds.

In a fourth aspect, the invention is directed to a method for incorporating crosslinking into a fluoropolymer composite material. The method includes reacting crosslinkable groups residing on a fluoropolymer and/or surface of a particulate composition when both the fluoropolymer and particulate composition are in a combined state during the reacting step. The crosslinking can be made to occur between fluoropolymer crosslinkable and particulate crosslinkable groups, or between fluoropolymer crosslinkable groups, or between particulate crosslinkable groups, or any combination thereof.

In a fifth aspect, the invention is directed to an article of manufacture constructed of a material containing the fluoropolymer composite material described above. The article can be, for example, a printing roller, tube, hose, sheet, fitted cover, protective cover, sleeve, film, block, ring, ball, part of an electrical component, or part of a medical device.

As shown, the invention advantageously provides a fluoropolymer composite material with improved thermal characteristics and a resulting longer usable life. The invention also advantageously provides new fluoroionic compounds and particulate compositions useful for, inter alia, synthesizing the fluoropolymer composites.

DETAILED DESCRIPTION OF THE INVENTION

Figure 1:
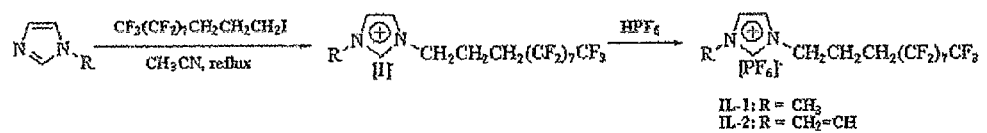
FIG. 1. General schematic showing a preferred method for synthesis of fluoroionic liquids.

In a first aspect, the present invention is directed to a new class of ionic compounds containing fluorine substitution of hydrogen atoms (i.e., fluoroionic compounds). The ionic compounds contain an imidazolium ring with a charge of +1. The various applications to which these ionic compounds can be useful include, for example, their use as conductive electrolytes, antistatic agents, non-volatile and environmentally friendly solvents, absorbents, and gas storage chemicals.

By one embodiment, the ionic compounds are according to the formula:

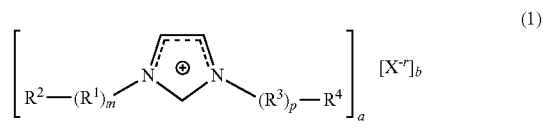

(1)

In formula (1), $R^1$ and $R^3$ can be, independently, hydrocarbon linking groups each having at least one carbon atom. In a first embodiment, the hydrocarbon linking groups are composed solely of carbon and hydrogen.

The hydrocarbon linking groups can have a maximum of, for example, 30 carbon atoms for most applications. In specific embodiments, the hydrocarbon linking groups can preferably contain within about 1 to 10, 1 to 8, or 1 to 6 carbon atoms. In other embodiments, the hydrocarbon linking groups can preferably contain 2 to 10, 2 to 8, or 2 to 6 carbon atoms.

The hydrocarbon linking groups of $R^1$ and $R^3$ can be saturated and straight-chained, i.e., straight-chained alkylene linking groups. Some examples of suitable straight-chained alkylene linking groups include those described by the formula $-(CH_2)_t-$ wherein t is at least 1 and preferably not more than about 30 for most applications, and more preferably not more than about 6 when applied as ionic liquids. Some examples of straight-chained alkylene linking groups include methylene ($-CH_2-$), ethylene ($-CH_2CH_2-$), trimethylene ($-CH_2CH_2CH_2-$), tetramethylene ($-CH_2CH_2CH_2CH_2-$), pentamethylene ($-CH_2CH_2CH_2CH_2CH_2-$), and hexamethylene ($-CH_2CH_2CH_2CH_2CH_2CH_2-$).

The hydrocarbon linking groups of $R^1$ and $R^3$ can alternatively be saturated and branched, i.e., branched alkylene linking groups. Some examples of suitable branched alkylene linking groups include $-CH(CH_3)-$, $-C(CH_3)_2-$, $-CH_2CH(CH_3)-$, $-CH_2C(CH_3)_2-$, $-CH(CH_3)C(CH_3)_2-$, $-C(CH_3)_2C(CH_3)_2-$, $-CH_2CH(CH_3)CH_2-$, and $-CH_2C(CH_3)_2CH_2-$, where groups in parentheses are not directly engaged in linking, but attached to a linking carbon atom.

The hydrocarbon linking groups of $R^1$ and $R^3$ can alternatively be saturated and cyclic, i.e., cycloalkylene linking groups. Some examples of cycloalkylene linking groups include 1,2-cyclopentadiyl, 1,2-cyclohexadiyl, and 1,4-cyclohexadiyl.

The hydrocarbon linking groups of $R^1$ and $R^3$ can alternatively be unsaturated. By being unsaturated, the linking groups have a minimum of one carbon-carbon double or triple bond. For example, the linking groups can be straight-chained, i.e., straight-chained alkenyl or alkynyl linking groups. Some examples of such groups include $-CH=CH-$, $-CH=CHCH_2-$, $-CH_2CH=CHCH_2-$, $-CH_2CH_2CH=CH-$, $-C\equiv C-$ and $-CH_2C\equiv CCH_2-$. The linking groups can be, in addition, branched, i.e., branched alkenyl or alkynyl linking groups. Some examples of such groups include $-C(CH_3)=CH-$, $-C(CH_3)=C(CH_3)-$, $-CH=C(CH_3)CH_2-$, $-C(CH_3)=CHCH_2-$, $-C(CH_3)=C(CH_3)CH_2-$, $-CH_2C(CH_3)=CHCH_2-$, $-CH_2C(CH_3)=C(CH_3)CH_2-$, $-CH(CH_3)C\equiv CCH_2-$, and $-CH(CH_3)C\equiv CCH(CH_3)-$. An unsaturated linking group can also be cyclic, such as, for example, cyclohex-2-en-1,4-diyl or cyclohex-2,5-diene-1,4-diyl. The cyclic unsaturated linking group can also be an aromatic linking ring or ring system, such as, for example, 1,2-phenylene, 1,4-phenylene, 2,6-dimethyl-1,4-phenylene, 4,4'-biphenylene, 4,4'-dimethylene-1,1'-biphenyl ($-CH_2-C_6H_4-C_6H_4-CH_2-$), diphenylmethane-4,4'-diyl ($-C_6H_4-CH_2-C_6H_4-$), stilbenzyl ($-C_6H_4-CH=CH-C_6H_4-$), and divinylenephenylene ($-CH=CH-C_6H_4-CH=CH-$).

By another embodiment, the hydrocarbon linking groups $R^1$ and $R^3$ can include one or more non-fluoro heteroatoms or heteroatom-containing groups. Some examples of such heteroatoms include oxygen (O), nitrogen (N), and sulfur (S). In one instance, a heteroatom interrupts a carbon-carbon link in the hydrocarbon linking group. Some examples of interrupting heteroatoms include $-O-$, $-NH-$, $-N=$, or $-S-$. The heteroatoms can also interrupt the hydrocarbon chain in a repetitive manner, such as in linking groups of the form $-(CH_2E)_t-$, $-(CH_2CH_2E)_t-$, or $-(CH_2CH_2CH_2E)_t-$ where E represents O, S, or NH and t is greater than 1 and up to, for example, 10, 20, or a higher number of units. In another instance, a heteroatom substitutes a hydrogen atom of the hydrocarbon linking group. Some examples of substituting heteroatoms include $-OH$, $-NH_2$, $-SH$, and Cl.

A heteroatom-containing group contains at least one heteroatom bound to one or more atoms other than hydrogen. In one instance, the heteroatom-containing group interrupts a carbon-carbon link in the hydrocarbon linking group. Some examples of interrupting heteroatom-containing groups include carbonyl $-C(O)-$, carboxy $-C(O)O-$, amido $-C(O)NH-$, urea $-NHC(O)NH-$, carbamate $-NHC(O)O-$, sulfoxide $-S(O)-$, sulfonyl $-S(O)_2-$, and diazene $-N=N-$. In another instance, the heteroatom-containing group substitutes a hydrogen atom of the hydrocarbon linking group. Some examples of substituting heteroatom-containing groups include aldehyde (e.g., $-C(O)H$), ketones (e.g., $-C(O)CH_3$), carboxylic acid $-C(O)OH$, esters (e.g., $-C(O)OCH_3$), amides (e.g., $C(O)NH_2$ or $C(O)NH(CH_3)$), ethers (e.g., $-OCH_3$), substituted amines (e.g., $-NH(CH_3)$ or $-N(CH_3)_2$), nitrile ($-CN$), nitro ($NO_2$), sulfonate ($-SO_3^-$), carboxylate ($-CO_2^-$).

The $R^1$ and $R^3$ hydrocarbon linking groups, described above, can be present or absent as indicated by the appended subscripts m and p, respectively. The subscripts m and p are independently 0 or 1, where a value of 0 for a subscript represents the absence of a group to which the subscript is appended, and a value of 1 represents the presence of a group to which the subscript is appended.

In formula (1), $R^2$ can be a hydrogen atom. When $R^2$ is a hydrogen atom, and when $R^1$ is present (m=1) without heteroatom substitution, then $-R^1-R^2$ represents a hydrocarbon group. The hydrocarbon group can be derived from any of the $R^1$ hydrocarbon linking groups described above where one end of the linking group is connected to a hydrogen atom.

For example, $-R^1-R^2$ can represent a saturated straight-chained hydrocarbon group. Some examples of such groups include methyl, ethyl, n-propyl, n-butyl, n-pentyl, n-hexyl, n-heptyl, n-octyl, n-nonyl, n-decyl, and the like. Alternatively, $-R^1-R^2$ can represent a saturated branched hydrocarbon group. Some examples of such groups include isopropyl, isobutyl, sec-butyl, t-butyl, 2-pentyl, 3-pentyl, 3-methylbutyl (isopentyl), 2,2-dimethylpropyl(neopentyl), 1,2-dimethylpropyl, 2-methylbutyl, 3-methylpentyl, 4-methylpentyl, and the like. Alternatively, $-R^1-R^2$ can represent a saturated cyclic hydrocarbon group. Some examples of such groups include cyclopropyl, cyclobutyl, cyclopentyl, cyclohexyl, and cycloheptyl.

Alternatively, $-R^1-R^2$ can represent an unsaturated straight-chained hydrocarbon group. Some examples of such groups include vinyl, 2-propen-1-yl, 3-buten-1-yl, 4-penten-1-yl, 5-hexen-1-yl, 6-hepten-1-yl, 2-buten-1-yl, 2-penten-1-yl, 3-penten-1-yl, 2,4-pentadienyl, 2,4,6-heptatrienyl, ethynyl, 2-propyn-1-yl(propargyl), 3-butyn-1-yl, 4-pentyn-1-yl, 2-butyn-1-yl, and the like. Alternatively, $-R^1-R^2$ can represent an unsaturated branched group. Some examples of such groups include propen-2-yl, 1-buten-2-yl, 1-buten-3-yl, 1-buten-2-methyl-3-yl, 1-buten-3-methyl-3-yl, 2-buten-2-methyl-3-yl.

The group $-R^1-R^2$ can alternatively represent an unsaturated cyclic hydrocarbon group. Some examples of such groups include 1-cyclopenten-1-yl, 1-cyclopenten-3-yl, 1-cyclopenten-4-yl, 3,4-dimethyl-3-cyclopenten-1-yl, 2,4-cyclopentadien-1-yl, 1-cyclohexen-1-yl, 1-cyclohexen-3-yl, 1-cyclohexen-4-yl, and 2,5-cyclohexadien-1-yl. The unsaturated cyclic hydrocarbon group can also be an aromatic ring, such as phenyl.

The group $-R^1-R^2$ can also represent a ring system. The ring system includes more than one ring, wherein the rings are directly or indirectly connected. When the rings are connected, they can be, for example, fused, connected by a bond, or form a bicyclic, tricyclic, or higher ring system. Some examples of hydrocarbon fused ring systems include naphthalenyl, anthracenyl, phenanthrenyl, and indenyl. An example of a bond-connected ring system includes biphenyl. Some examples of hydrocarbon bicyclic ring systems include bicyclo[4.4.0]decanyl(decalinyl), bicyclo[2.2.1]heptanyl (norbornyl), and norbornenyl.

In another embodiment, $R^2$ is a hydrogen atom, and $R^1$ is present (m=1) and includes insertion or hydrogen-atom substitution by one or more heteroatoms. In such a case, —$R^1$-$R^2$ represents a heteroatom-substituted hydrocarbon group. The heteroatom-substituted group can be, for example, any of the heteroatom-substituted linker groups $R^1$, as described above, wherein the capping group $R^2$ is a hydrogen atom. The heteroatom-substituted group can also be, for example, any of the hydrocarbon groups described above when $R^1$ is a hydrocarbon linker group, wherein the groups have been modified by insertion or hydrogen-atom substitution by one or more heteroatoms. For example, the hydrocarbon rings and ring systems described above can also include one or more ring heteroatoms or heteroatom-containing groups. For the case of rings, the heteroatoms more commonly include the heteroatoms N, O, and S. Some examples of heteroatom-containing rings and ring systems include pyrrolyl, pyrrolidinyl, imidazolyl, pyrazolyl, piperidinyl, N-methylpiperidinyl, pyridinyl, piperazinyl, pyrazinyl, pyrimidinyl, triazinyl, oxazolyl, morpholinyl, thiopheneyl, indolyl, purinyl, and furanyl.

In formula (1), $R^2$ can also be a fluoro-substituted hydrocarbon group having at least one carbon atom and at least one fluorine atom. For many applications, particularly when the ionic compound is desired to be an ionic liquid or viscous solid, a maximum carbon number of about 30 is sufficient. The fluoro-substituted hydrocarbon group of $R^2$ is properly described by reference to the hydrocarbon groups described above for —$R^1$-$R^2$ and making the modification that at least one hydrogen atom of any of the classes or specific examples described therein be substituted by a fluorine atom.

In a first embodiment, the fluoro-substituted hydrocarbon group of $R^2$ does not contain any non-fluoro heteroatoms. Some examples of such $R^2$ groups include fluoromethyl (—$CH_2F$), difluoromethyl (—$CHF_2$), trifluoromethyl (i.e., perfluoromethyl, $CF_3$), fluoroethyl (—$CH_2CH_2F$ or —$CHFCH_3$), difluoroethyl (—$CH_2CHF_2$ or $CHFCH_2F$ or —$CF_2CH_3$), trifluoroethyl (—$CH_2CF_3$ or —$CHFCHF_2$ or $CF_2CH_2F$), tetrafluoroethyl (—$CHFCF_3$ or —$CF_2CHF_2$), perfluoroethyl (—$CF_2CF_3$), fluoropropyl (—$CH_2CH_2CH_2F$ or —$CH(CH_3)CH_2F$ or —$CHFCH_2CH_3$), difluoropropyl (e.g., —$CH_2CHFCHF$), trifluoropropyl (e.g., —$CHFCHFCH_2F$ or —$CH(CF_3)CH_3$), tetrafluoropropyl (e.g., —$CHFCHFCHF_2$), pentafluoropropyl (e.g., —$CHFCHFCF_3$), hexafluoropropyl (e.g., —$CHFCF_2CF_3$ or —$CH(CF_3)_2$), perfluoropropyl (e.g., —$CF_2CF_2CF_3$ or —$CF(CF_3)_2$), perfluorobutyl (—$(CF_2)_3CF_3$ or —$CF(CF_3)CF_2CF_3$ or —$CF_2CF(CF_3)_2$ or —$C(CF_3)_3$), perfluoropentyl (e.g., —$(CF_2)_4CF_3$), perfluorohexyl (e.g., —$(CF_2)_5CF_3$), perfluoroheptyl, perfluorooctyl, perfluorononyl, perfluorodecyl, perfluorododecyl, perfluorododecyl, perfluorotridecyl, perfluorotetradecyl, perfluoropentadecyl, perfluorohexadecyl, perfluoroheptadecyl, perfluorooctadecyl, fluorovinyl (—$CH=CHF$ or —$CF=CH_2$), difluorovinyl (—$CH=CF_2$ or —$CF=CHF$), trifluorovinyl (—$CF=CF_2$), difluoropropenyl (e.g., —$CF=CF(CH_3)$), trifluoropropenyl (e.g., —$CH=CH(CF_3)$), pentafluoropropenyl (e.g., —$CF=CF(CF_3)$, —$C(CF_3)=CF_2$, or —$CF_2CF=CF_2$), hexafluorobutenyl (e.g., —$CH_2C(CF_3)=CH(CF_3)$), perfluorobutenyl (e.g., —$CF_2CF_2CF=CF_2$ or —$CF_2CF=CFCF_3$), branched hexafluoropentenyl (e.g., —$CH_2C(CF_3)=CH(CF_3)$ or —$CH_2$—$CH=C(CF_3)_2$)), trifluoromethylethynyl (—$C≡C$—$CF_3$), trifluoromethylpropargyl (e.g., —$CH_2C≡C$—$CF_3$), pentafluoro-1,3-butadienyl (—$CF=CFCF=CF_2$), fluorocyclopentyl, fluorocyclohexyl, difluorocyclohexyl, perfluorocyclohexyl, fluorophenyl, difluorophenyl, trifluorophenyl, tetrafluorophenyl, pentafluorophenyl, trifluoromethylphenyl, and bis(trifluoromethyl)phenyl.

In a second embodiment, the fluoro-substituted hydrocarbon group of $R^2$ contains one or more non-fluoro heteroatoms or heteroatom-containing groups. Some examples of such $R^2$ groups include —$OCF_3$, —$OCF_2CF_3$, —$(OCF_2)_xR$, —$(OCF_2CF_2)_xR$, —$(OCF(CF_3)CF_2)_xR$, —$(CF_2CF_2O)_xR$, —$(CF(CF_3)CF_2O)_xR$, —$[CF_2CF(OR)]_xR$, where x is preferably from about 1 to 20 and R is independently hydrogen or any of the hydrocarbon or fluoro-substituted hydrocarbon groups described above, —$CF_2OCF_3$, —$CF_2CF_2OCF_3$, —$CF_2CF_2OCF_2CF_3$, —$OC_6F_5$, —$C_6F_4OR$, —$OCF=CF_2$, —$OCH_2$—$CF=CF_2$, —$OCH_2CH(CF_3)CH_3$, —$NH(CF_3)$, —$N(CF_3)_2$, —$NH(CF_2)_7CF_3$, —$N[(CF_2)_7CF_3]_2$, —$NH(CF_2CF_2OR)$, —$N(CF_2CF_2OR)_2$, —$N^+(CF_3)$, —$S(O)_2CF_3$, —$CF_2S(O)_2CF_2CF_3$, —$N=CF_2$, 4-fluoropyridinium, 4-trifluoromethylpiperazinyl, 4-perfluorooctyl-piperazinium, —$Si(CF_3)_3$, —$Si(OCF_3)_3$, —$SiR_2(CF_2)_7CF_3$, —$SiR_2(OCF_3)_2$, —$CH_2CH_2C(O)OCF_3$, —$CH_2CH_2C(O)OC_6F_{10}$, —$CH_2CH_2C(O)OC_6F_5$, —$SCF_3$, and —$SCF_2CF_3$.

In a particular embodiment, $R^1$ represents one or more additional imidazole or imidazolium rings interconnected by one or more linkers, the length and composition of each linker being independent. For example, $R^1$ can represent an imidazolium ring connected indirectly by one of its ring nitrogen atoms through a hydrocarbon linker to the ring nitrogen shown in FIG. 1. Alternatively, R1 can represent for example, two, three, four, or a higher number of imidazole or imidazolium rings each interconnected by a linker, wherein one of the imidazole rings therein is connected indirectly by one of its ring nitrogen atoms through a hydrocarbon linker to the ring nitrogen atom shown in FIG. 1. $R^2$ is any suitable group as described above, that caps the $R^1$ linker containing the one or more imidazole rings.

In formula (1), $R^2$ can also simply be a heteroatom-containing group only when m is 1. In this embodiment, $R^2$ functions as a heteroatom endcapping group in the —$R^1$-$R^2$ combined group, and therefore, the combined group —$R^1$-$R^2$ can aptly be described as an endcapped hydrocarbon group. The applicable heteroatom-containing groups have already been described above. Some examples of —$R^1$-$R^2$ in this embodiment include —$R^1$—OH, $R^1$—$NH_2$, $R^1$—$NH_3^+$, $R^1$—$NH(CH_3)$, $R^1$—$N(CH_3)_2$, $R^1$—C(O)H, $R^1$—C(O)OH, $R^1$—$C(O)NH_2$, $R^1$—$S(O)_2OH$, $R^1$—CN, $R^1$—F, $R^1$—Cl, $R^1$—Br, $R^1$—$NO_2$, $R^1$—OCN, and $R^1$—NCO, where $R^1$ can be any of the substituted or non-substituted hydrocarbon groups described above.

In one embodiment, the —$R^1$-$R^2$ combined group does not include a dichlorophenyl group. In another embodiment, the —$R^1$-$R^2$ combined group may include one such group but does not include two dichlorophenyl groups. In another embodiment, the —$R^1$-$R^2$ combined group may include two such groups but does not include that the two dichlorophenyl groups are interconnected by an oxyalkylene spacer, such as —$CH_2OCH_2$—. In a more particular embodiment, the —$R^1$-$R^2$ combined group is not a [2-(2,4-dichlorophenyl)-2-(2,4-dichlorobenzyloxy)]ethyl-1-yl group.

In formula (1), $R^4$ is a fluoro-substituted hydrocarbon group having at least one carbon atom and at least one fluorine atom and optionally including one or more non-fluoro heteroatoms or heteroatom-containing groups. All of the fluoro-substituted hydrocarbon groups already described above for $R^2$ are applicable to $R^4$ (i.e., $R^4$ is aptly described by all of the fluoro-substituted hydrocarbon groups already described for $R^2$). In some embodiments, $R^4$ can have a maximum of, for example, 30 carbon atoms for most applications. In other embodiments, $R^4$ can preferably contain within about 4 to 12, or 6 to 10, carbon atoms.

$X^{-r}$ represents an anion with negative charge $-r$, where $r$ typically assumes a value of 1, 2, or 3. In order to preserve charge neutrality, the subscripts a and b are positive integers such that a=b×r. Some examples of suitable counteranions include the halides (e.g., fluoride, chloride, bromide, iodide), $PF_6^-$, $BF_4^-$, bistriflimide[$(CF_3SO_2)_2N$]$^-$, triflate ($CF_3SO_3^-$), tosylate, nitrate, borate, chlorate, perchlorate, bromate, perbromate, iodate, periodate, aluminates, phosphates, sulfate, bisulfate, sulfonates, hydroxide, formate, oxalate, acetate, glycolate, propionate, butyrate, succinate, malonate, fumarate, citrate, terephthalate, phthalate, and glutarate.

In a first embodiment, formula (1) refers to the class of imidazolium compounds wherein $R^1$ and $R^3$ linking groups are absent. A 1,3-di-(fluorohydrocarbon) imidazolium subclass of compounds results when $R^2$ is a fluorosubstituted hydrocarbon group. Some examples of these types of compounds include the salts of 1,3-bis(perfluoromethyl) imidazolium, 1,3-bis(perfluoroethyl)imidazolium, 1,3-bis-(perfluorooctyl)imidazolium, 1-perfluorooctyl-3-perfluoromethylimidazolium, and 1-perfluorooctyl-3-perfluoropropylimidazolium.

A 1-(H)-3-fluorohydrocarbon imidazolium subclass of compounds results when $R^2$ is a hydrogen atom. Some examples of these types of compounds include the salts of 1-perfluoromethyl-3-H-imidazolium, 1-perfluoroethyl-3-H-imidazolium, 1-perfluoropropyl-3-H-imidazolium, 1-perfluorobutyl-3-H-imidazolium, 1-perfluoropentyl-3-H-imidazolium, 1-perfluorohexyl-3-H-imidazolium, 1-perfluoroheptyl-3-H-imidazolium, 1-perfluorooctyl-3-H-imidazolium, 1-perfluorododecyl-3-H-imidazolium, and 1-perfluorohexadecyl-3-H-imidazolium.

In a second embodiment, formula (1) refers to the class of imidazolium compounds wherein $R^3$ remains absent, $R^1$ is present, and $R^2$ is a hydrogen atom. In this class, —$R^1$-$R^2$ represents a hydrocarbon group, and therefore, this class of compounds represents a 1-fluorohydrocarbon-3-hydrocarbon imidazolium class of compounds. Some examples of these types of compounds include the salts of 1-perfluoromethyl-3-methylimidazolium, 1-perfluoroethyl-3-methylimidazolium, 1-perfluorodecyl-3-methylimidazolium, 1-perfluorooctyl-3-propylimidazolium, 1-perfluoromethyl-3-isopropylimidazolium, 1-perfluorododecyl-3-isopropylimidazolium, 1-perfluorooctyl-3-butylimidazolium, 1-perfluorooctyl-3-isobutylimidazolium, 1-perfluoromethyl-3-vinylimidazolium, 1-perfluorobutyl-3-vinylimidazolium, 1-perfluorooctyl-3-vinylimidazolium, 1-perfluorooctyl-3-allylimidazolium, 1-perfluorodecyl-3-(3-butenyl)imidazolium, and 1-perfluorooctyl-3-phenylimidazolium.

In a third embodiment, formula (1) refers to the class of imidazolium compounds wherein $R^3$ remains absent, $R^1$ is present, and $R^2$ is a fluorohydrocarbon group. In this case, —$R^1$-$R^2$ represents a (hydrocarbon linker)-fluorohydrocarbon group. Therefore, these compounds belong to the 1-fluorohydrocarbon-3-(hydrocarbon-fluorohydrocarbon)imidazolium class of compounds. Some examples of these types of compounds include the salts of 1-perfluoromethyl-3-(2,2,2-trifluoroethyl)imidazolium, 1-perfluoroethyl-3-(2,2,2-trifluoroethyl)imidazolium, 1-perfluoroisopropyl-3-(2,2,2-trifluoroethyl)imidazolium, 1-perfluoroisobutyl-3-(2,2,3,3,4,4,4-heptafluorobutyl)imidazolium, 1-perfluorooctyl-3-(perfluorooctylmethyl)imidazolium, 1-perfluoropropyl-3-(3-perfluorododecylpropyl)imidazolium, 1-perfluoromethyl-3-(6-perfluoropropylhexyl)imidazolium, 1-perfluoropropyl-3-(8-perfluorooctyloctyl)imidazolium, and 1-perfluorotetradecyl-3-(6-perfluorooctylhexyl)imidazolium.

In a fourth embodiment, formula (1) refers to the class of imidazolium compounds wherein $R^1$ and $R^3$ are both present and $R^2$ is a fluorohydrocarbon group. In this class, —$R^1$-$R^2$ and —$R^3$-$R^4$ each independently represents a (hydrocarbon linker)-fluorohydrocarbon group. Therefore, these compounds belong to the 1,3-(hydrocarbon-fluorohydrocarbon) imidazolium class of compounds. Some examples of these types of compounds include the salts of bis-1,3-(2,2,2-trifluoroethyl)imidazolium, 1-(3-perfluoropropylpropyl)-3-(2,2,2-trifluoroethyl)imidazolium, bis-1,3-(4-perfluoromethylbutyl)imidazolium, bis-1,3-(8-perfluoromethyloctyl)imidazolium, bis-1,3-(3-perfluorooctylpropyl)imidazolium, bis-1,3-(2-perfluorodecylethyl)imidazolium, 1-(2,2,2-trifluoroethyl)-3-(12-perfluoroethyldodecyl)imidazolium, 1-(3-perfluoromethylpropyl)-3-(3-perfluorooctylpropyl)imidazolium, bis-1,3-(6-perfluorooctylhexyl)imidazolium, and bis-1,3-(2-perfluorotetradecylethyl)imidazolium.

In a fifth embodiment, formula (1) refers to the class of imidazolium compounds wherein $R^1$ and $R^3$ are both present and $R^2$ is a hydrogen atom. In this case, —$R^1$-$R^2$ represents a hydrocarbon group. Therefore, these compounds belong to the 1-(hydrocarbon-fluorohydrocarbon)-3-hydrocarbon imidazolium class of compounds. A subclass of these compounds can be conveniently described according to formula (3) below.

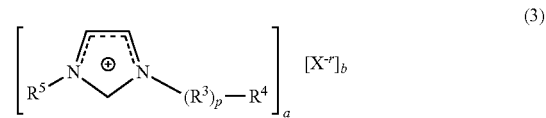

(3)

In formula (3), —$R^1$-$R^2$ has been replaced with $R^5$, where $R^5$ is a hydrocarbon group. $R^5$ preferably contains about 1 to 6 carbon atoms. The linking group $R^3$ also preferably contains about 1 to 6 carbon atoms. The group $R^4$ is a fluoro-substituted hydrocarbon group, as already defined above.

Some examples of these types of compounds include the salts of 1-(2-fluoroethyl)-3-methylimidazolium, 1-(2,2,2-trifluoroethyl)-3-methylimidazolium, 1-(2,2,2-trifluoroethyl)-3-ethylimidazolium, 1-(2,2,2-trifluoroethyl)-3-ethylimidazolium, 1-(2,2,2-trifluoroethyl)-3-propylimidazolium, 1-(2,2,2-trifluoroethyl)-3-isopropylimidazolium, 1-(2,2,2-trifluoroethyl)-3-butylimidazolium, 1-(2,2,2-trifluoroethyl)-3-isobutylimidazolium, 1-(3-perfluoroethylpropyl)-3-methylimidazolium, 1-(3-perfluorooctylpropyl)-3-methyl imidazolium, 1-(3-perfluorodecylpropyl)-3-methylimidazolium, 1-(3-perfluorotetradecylpropyl)-3-methylimidazolium, 1-(2,2,2-trifluoroethyl)-3-octylimidazolium, 1-(2-perfluorotetradecylethyl)-3-isopentylimidazolium, 1-(2-perfluoropropylethyl)-3-dodecylimidazolium, 1-(3-perfluoroethylpropyl)-3-vinylimidazolium, 1-(3-perfluoroodylpropyl)-3-vinyl imidazolium, 1-(3-perfluorooctylpropyl)-3-benzyl imidazolium, 1-(3-perfluoroodylpropyl)-3-(3-butenyl) imidazolium, 1-(3-perfluorooctylpropyl)-3-cyclohexylimidazolium, 1-(3-perfluorodecylpropyl)-3-vinylimidazolium, 1-(3-perfluorotetradecylpropyl)-3-vinylimidazolium, and 1-(2,2,2-trifluoroethyl)-3-(7-octenyl)imidazolium.

Table 1, as shown below, lists numerous exemplary ionic compounds according to the present invention.

TABLE 1

Exemplary compounds of the invention

| No. | Name of Imidazolium Portion of Compound | $R^1$ | $R^2$ | $R^3$ | $R^4$ |
|---|---|---|---|---|---|
| 1 | 1,3-bis(perfluoromethyl)imidazolium | absent | $CF_3$ | absent | $CF_3$ |
| 2 | 1-perfluoroethyl-3-perfluoromethylimidazolium | absent | $CF_3$ | absent | $CF_2CF_3$ |
| 3 | 1-perfluorohexyl-3-perfluoromethylimidazolium | absent | $CF_3$ | absent | $(CF_2)_5CF_3$ |
| 4 | 1-perfluorooctyl-3-perfluoromethylimidazolium | absent | $CF_3$ | absent | $(CF_2)_7CF_3$ |
| 5 | 1-perfluorohexadecyl-3-perfluoromethylimidazolium | absent | $CF_3$ | absent | $(CF_2)_{15}CF_3$ |
| 6 | 1,3-bis(perfluoroethyl)imidazolium | absent | $CF_2CF_3$ | absent | $CF_2CF_3$ |
| 7 | 1-perfluorobutyl-3-perfluoroethylimidazolium | absent | $CF_2CF_3$ | absent | $(CF_2)_3CF_3$ |
| 8 | 1,3-bis(perfluoropropyl)imidazolium | absent | $CF_2CF_2CF_3$ | absent | $CF_2CF_2CF_3$ |
| 9 | 1-perfluorooctyl-3-perfluoropropylimidazolium | absent | $CF_2CF_2CF_3$ | absent | $(CF_2)_7CF_3$ |
| 10 | 1,3-bis(perfluorobutyl)imidazolium | absent | $(CF_2)_3CF_3$ | absent | $(CF_2)_3CF_3$ |
| 11 | 1-perfluorooctyl-3-perfluorobutylimidazolium | absent | $(CF_2)_3CF_3$ | absent | $(CF_2)_7CF_3$ |
| 12 | 1,3-bis(perfluorohexyl)imidazolium | absent | $(CF_2)_5CF_3$ | absent | $(CF_2)_5CF_3$ |
| 13 | 1-perfluorooctyl-3-perfluorohexylimidazolium | absent | $(CF_2)_5CF_3$ | absent | $(CF_2)_7CF_3$ |
| 14 | 1-perfluorohexadecyl-3-perfluorohexylimidazolium | absent | $(CF_2)_5CF_3$ | absent | $(CF_2)_{15}CF_3$ |
| 15 | 1,3-bis(perfluorooctyl)imidazolium | absent | $(CF_2)_7CF_3$ | absent | $(CF_2)_7CF_3$ |
| 16 | 1,3-bis(perfluorododecyl)imidazolium | absent | $(CF_2)_{11}CF_3$ | absent | $(CF_2)_{11}CF_3$ |
| 17 | 1,3-bis(perfluorohexadecyl)imidazolium | absent | $(CF_2)_{15}CF_3$ | absent | $(CF_2)_{15}CF_3$ |
| 18 | 1-perfluoromethyl-3-methylimidazolium | —$CH_2$— | H | absent | $CF_3$ |
| 19 | 1-perfluoroethyl-3-methylimidazolium | —$CH_2$— | H | absent | $CF_2CF_3$ |
| 20 | 1-perfluoropropyl-3-methylimidazolium | —$CH_2$— | H | absent | $CF_2CF_2CF_3$ |
| 21 | 1-perfluorobutyl-3-methylimidazolium | —$CH_2$— | H | absent | $(CF_2)_3CF_3$ |
| 22 | 1-perfluorooctyl-3-methylimidazolium | —$CH_2$— | H | absent | $(CF_2)_7CF_3$ |
| 23 | 1-perfluorodecyl-3-methylimidazolium | —$CH_2$— | H | absent | $(CF_2)_9CF_3$ |
| 24 | 1-perfluorododecyl-3-methylimidazolium | —$CH_2$— | H | absent | $(CF_2)_{11}CF_3$ |
| 25 | 1-perfluorohexadecyl-3-methylimidazolium | —$CH_2$— | H | absent | $(CF_2)_{15}CF_3$ |
| 26 | 1-perfluorooctadecyl-3-methylimidazolium | —$CH_2$— | H | absent | $(CF_2)_{17}CF_3$ |
| 27 | 1-perfluoromethyl-3-ethylimidazolium | —$CH_2CH_2$— | H | absent | $CF_3$ |
| 28 | 1-perfluoroethyl-3-ethylimidazolium | —$CH_2CH_2$— | H | absent | $CF_2CF_3$ |
| 29 | 1-perfluorooctyl-3-ethylimidazolium | —$CH_2CH_2$— | H | absent | $(CF_2)_7CF_3$ |
| 30 | 1-perfluorododecyl-3-ethylimidazolium | —$CH_2CH_2$— | H | absent | $(CF_2)_{11}CF_3$ |
| 31 | 1-perfluoromethyl-3-propylimidazolium | —$(CH_2)_3$— | H | absent | $CF_3$ |
| 32 | 1-perfluoroethyl-3-propylimidazolium | —$(CH_2)_3$— | H | absent | $CF_2CF_3$ |
| 33 | 1-perfluorooctyl-3-propylimidazolium | —$(CH_2)_3$— | H | absent | $(CF_2)_7CF_3$ |
| 34 | 1-perfluorododecyl-3-propylimidazolium | —$(CH_2)_3$— | H | absent | $(CF_2)_{11}CF_3$ |
| 35 | 1-perfluoromethyl-3-isopropylimidazolium | —$C(CH_3)_2$— | H | absent | $CF_3$ |
| 36 | 1-perfluoroethyl-3-isopropylimidazolium | —$C(CH_3)_2$— | H | absent | $CF_2CF_3$ |
| 37 | 1-perfluorooctyl-3-isopropylimidazolium | —$C(CH_3)_2$— | H | absent | $(CF_2)_7CF_3$ |
| 38 | 1-perfluorododecyl-3-isopropylimidazolium | —$C(CH_3)_2$— | H | absent | $(CF_2)_{11}CF_3$ |
| 39 | 1-perfluoromethyl-3-butylimidazolium | —$(CH_2)_4$— | H | absent | $CF_3$ |
| 40 | 1-perfluoroethyl-3-butylimidazolium | —$(CH_2)_4$— | H | absent | $CF_2CF_3$ |
| 41 | 1-perfluorooctyl-3-butylimidazolium | —$(CH_2)_4$— | H | absent | $(CF_2)_7CF_3$ |
| 42 | 1-perfluorododecyl-3-butylimidazolium | —$(CH_2)_4$— | H | absent | $(CF_2)_{11}CF_3$ |
| 43 | 1-perfluorohexadecyl-3-butylimidazolium | —$(CH_2)_4$— | H | absent | $(CF_2)_{15}CF_3$ |
| 44 | 1-perfluoromethyl-3-isobutylimidazolium | isobutyl | H | absent | $CF_3$ |
| 45 | 1-perfluorooctyl-3-isobutylimidazolium | isobutyl | H | absent | $(CF_2)_7CF_3$ |
| 46 | 1-perfluoromethyl-3-t-butylimidazolium | t-butyl | H | absent | $CF_3$ |
| 47 | 1-perfluorooctyl-3-t-butylimidazolium | t-butyl | H | absent | $(CF_2)_7CF_3$ |
| 48 | 1-perfluoromethyl-3-pentylimidazolium | —$(CH_2)_5$— | H | absent | $CF_3$ |
| 49 | 1-perfluorooctyl-3-pentylimidazolium | —$(CH_2)_5$— | H | absent | $(CF_2)_7CF_3$ |
| 50 | 1-perfluoromethyl-3-isopentylimidazolium | isopentyl | H | absent | $CF_3$ |
| 51 | 1-perfluorooctyl-3-isopentylimidazolium | isopentyl | H | absent | $(CF_2)_7CF_3$ |
| 52 | 1-perfluorododecyl-3-isopentylimidazolium | isopentyl | H | absent | $(CF_2)_{11}CF_3$ |
| 53 | 1-perfluoromethyl-3-hexylimidazolium | —$(CH_2)_6$— | H | absent | $CF_3$ |
| 54 | 1-perfluorooctyl-3-hexylimidazolium | —$(CH_2)_6$— | H | absent | $(CF_2)_7CF_3$ |
| 55 | 1-perfluoromethyl-3-vinylimidazolium | vinyl | H | absent | $CF_3$ |
| 56 | 1-perfluoroethyl-3-vinylimidazolium | vinyl | H | absent | $CF_2CF_3$ |
| 57 | 1-perfluoropropyl-3-vinylimidazolium | vinyl | H | absent | $CF_2CF_2CF_3$ |
| 58 | 1-perfluorobutyl-3-vinylimidazolium | vinyl | H | absent | $(CF_2)_3CF_3$ |
| 59 | 1-perfluorooctyl-3-vinylimidazolium | vinyl | H | absent | $(CF_2)_7CF_3$ |
| 60 | 1-perfluorodecyl-3-vinylimidazolium | vinyl | H | absent | $(CF_2)_9CF_3$ |
| 61 | 1-perfluorododecyl-3-vinylimidazolium | vinyl | H | absent | $(CF_2)_{11}CF_3$ |
| 62 | 1-perfluorohexadecyl-3-vinylimidazolium | vinyl | H | absent | $(CF_2)_{15}CF_3$ |
| 63 | 1-perfluorooctadecyl-3-vinylimidazolium | vinyl | H | absent | $(CF_2)_{17}CF_3$ |
| 64 | 1-perfluoromethyl-3-phenylimidazolium | phenyl | H | absent | $CF_3$ |
| 65 | 1-perfluorooctyl-3-phenylimidazolium | phenyl | H | absent | $(CF_2)_7CF_3$ |
| 66 | 1-perfluorohexadecyl-3-phenylimidazolium | phenyl | H | absent | $(CF_2)_{15}CF_3$ |
| 67 | 1-perfluoromethyl-3-benzylimidazolium | benzyl | H | absent | $CF_3$ |
| 68 | 1-perfluorooctyl-3-benzylimidazolium | benzyl | H | absent | $(CF_2)_7CF_3$ |
| 69 | 1-perfluorohexadecyl-3-benzylimidazolium | benzyl | H | absent | $(CF_2)_{15}CF_3$ |
| 70 | 1-perfluoromethyl-3-(2,2,2-trifluoroethyl)imidazolium | —$CH_2$— | $CF_3$ | absent | $CF_3$ |
| 71 | 1-perfluoroethyl-3-(2,2,2-trifluoroethyl)imidazolium | —$CH_2$— | $CF_3$ | absent | $CF_2CF_3$ |
| 72 | 1-perfluoropropyl-3-(2,2,2-trifluoroethyl)imidazolium | —$CH_2$— | $CF_3$ | absent | $CF_2CF_2CF_3$ |
| 73 | 1-perfluorooctyl-3-(2,2,2-trifluoroethyl)imidazolium | —$CH_2$— | $CF_3$ | absent | $(CF_2)_7CF_3$ |

TABLE 1-continued

Exemplary compounds of the invention

| No. | Name of Imidazolium Portion of Compound | R$^1$ | R$^2$ | R$^3$ | R$^4$ |
|---|---|---|---|---|---|
| 74 | 1-perfluorododecyl-3-(2,2,2-trifluoroethyl)imidazolium | —CH$_2$— | CF$_3$ | absent | (CF$_2$)$_{11}$CF$_3$ |
| 75 | 1-perfluorooctyl-3-(2,2,3,3,3-pentafluoropropyl)imidazolium | —CH$_2$— | CF$_2$CF$_3$ | absent | (CF$_2$)$_7$CF$_3$ |
| 76 | 1-perfluorotetradecyl-3-(2,2,3,3,3-pentafluoropropyl)imidazolium | —CH$_2$— | CF$_2$CF$_3$ | absent | (CF$_2$)$_{13}$CF$_3$ |
| 77 | 1-perfluorooctyl-3-(2,2,3,3,4,4,4-heptafluorobutyl)imidazolium | —CH$_2$— | CF$_2$CF$_2$CF$_3$ | absent | (CF$_2$)$_7$CF$_3$ |
| 78 | 1-perfluorododecyl-3-(2,2,3,3,4,4,4-heptafluorobutyl)imidazolium | —CH$_2$— | CF$_2$CF$_2$CF$_3$ | absent | (CF$_2$)$_{11}$CF$_3$ |
| 79 | 1-perfluorooctyl-3-(perfluorobutylmethyl)imidazolium | —CH$_2$— | (CF$_2$)$_3$CF$_3$ | absent | (CF$_2$)$_7$CF$_3$ |
| 80 | 1-perfluorooctyl-3-(perfluorooctylmethyl)imidazolium | —CH$_2$— | (CF$_2$)$_7$CF$_3$ | absent | (CF$_2$)$_7$CF$_3$ |
| 81 | 1-perfluoromethyl-3-(2-perfluorobutylethyl)imidazolium | —CH$_2$CH$_2$— | (CF$_2$)$_3$CF$_3$ | absent | CF$_3$ |
| 82 | 1-perfluoroethyl-3-(2-perfluorobutylethyl)imidazolium | —CH$_2$CH$_2$— | (CF$_2$)$_3$CF$_3$ | absent | CF$_2$CF$_3$ |
| 83 | 1-perfluoropropyl-3-(2-perfluorohexylethyl)imidazolium | —CH$_2$CH$_2$— | (CF$_2$)$_5$CF$_3$ | absent | CF$_2$CF$_2$CF$_3$ |
| 84 | 1-perfluorooctyl-3-(2-perfluorohexylethyl)imidazolium | —CH$_2$CH$_2$— | (CF$_2$)$_5$CF$_3$ | absent | (CF$_2$)$_7$CF$_3$ |
| 85 | 1-perfluoromethyl-3-(3-perfluorohexylpropyl)imidazolium | —(CH$_2$)$_3$— | (CF$_2$)$_5$CF$_3$ | absent | CF$_3$ |
| 86 | 1-perfluoroethyl-3-(3-perfluorooctylpropyl)imidazolium | —(CH$_2$)$_3$— | (CF$_2$)$_7$CF$_3$ | absent | CF$_2$CF$_3$ |
| 87 | 1-perfluoropropyl-3-(3-perfluorododecylpropyl)imidazolium | —(CH$_2$)$_3$— | (CF$_2$)$_{11}$CF$_3$ | absent | CF$_2$CF$_2$CF$_3$ |
| 88 | 1-perfluorooctyl-3-(3-perfluorohexadecylpropyl)imidazolium | —(CH$_2$)$_3$— | (CF$_2$)$_{15}$CF$_3$ | absent | (CF$_2$)$_7$CF$_3$ |
| 89 | bis-1,3-(2,2,2-trifluoroethyl)imidazolium | —CH$_2$— | CF$_3$ | —CH$_2$— | CF$_3$ |
| 90 | 1-(2,2,3,3,3-pentafluoropropyl)-3-(2,2,2-trifluoroethyl)imidazolium | —CH$_2$— | CF$_3$ | —CH$_2$— | CF$_2$CF$_3$ |
| 91 | 1-(perfluorobutylmethyl)-3-(2,2,2-trifluoroethyl)imidazolium | —CH$_2$— | CF$_3$ | —CH$_2$— | CF$_2$CF$_2$CF$_3$ |
| 92 | 1-(perfluorooctylmethyl)-3-(2,2,2-trifluoroethyl)imidazolium | —CH$_2$— | CF$_3$ | —CH$_2$— | (CF$_2$)$_7$CF$_3$ |
| 93 | 1-(perfluorododecylmethyl)-3-(2,2,2-trifluoroethyl)imidazolium | —CH$_2$— | CF$_3$ | —CH$_2$— | (CF$_2$)$_{11}$CF$_3$ |
| 94 | 1-(perfluorooctadecylmethyl)-3-(2,2,2-trifluoroethyl)imidazolium | —CH$_2$— | CF$_3$ | —CH$_2$— | (CF$_2$)$_{17}$CF$_3$ |
| 95 | 1-(3-perfluorooctylpropyl)-3-(2,2,3,3,3-pentafluoropropyl)imidazolium | —CH$_2$— | CF$_2$CF$_3$ | —(CH$_2$)$_3$— | (CF$_2$)$_7$CF$_3$ |
| 96 | 1-(2-perfluorooctylethyl)-3-(2,2,3,3,3-pentafluoropropyl)imidazolium | —CH$_2$— | CF$_2$CF$_3$ | —CH$_2$CH$_2$— | (CF$_2$)$_7$CF$_3$ |
| 97 | 1-(2-perfluorooctylethyl)-3-(perfluoropropylmethyl)imidazolium | —CH$_2$— | CF$_2$CF$_2$CF$_3$ | —CH$_2$CH$_2$— | (CF$_2$)$_7$CF$_3$ |
| 98 | 1-(3-perfluorooctylpropyl)-3-(perfluoropropylmethyl)imidazolium | —CH$_2$— | CF$_2$CF$_2$CF$_3$ | —(CH$_2$)$_3$— | (CF$_2$)$_7$CF$_3$ |
| 99 | 1-(2-perfluorooctylethyl)-3-(perfluorobutylmethyl)imidazolium | —CH$_2$— | (CF$_2$)$_3$CF$_3$ | —CH$_2$CH$_2$— | (CF$_2$)$_7$CF$_3$ |
| 100 | 1-(perfluorooctylmethyl)-3-(perfluorooctylmethyl)imidazolium | —CH$_2$— | (CF$_2$)$_7$CF$_3$ | —CH$_2$— | (CF$_2$)$_7$CF$_3$ |
| 101 | 1-(4,4,4-trifluorobutyl)-3-(2-perfluorobutylethyl)imidazolium | —CH$_2$CH$_2$— | (CF$_2$)$_3$CF$_3$ | —(CH$_2$)$_3$— | CF$_3$ |
| 102 | bis-1,3-(2-perfluorobutylethyl)imidazolium | —CH$_2$CH$_2$— | (CF$_2$)$_3$CF$_3$ | —CH$_2$CH$_2$— | (CF$_2$)$_3$CF$_3$ |
| 103 | 1-(2-perfluoropropylethyl)-3-(2-perfluorohexylethyl)imidazolium | —CH$_2$CH$_2$— | (CF$_2$)$_5$CF$_3$ | —CH$_2$CH$_2$— | CF$_2$CF$_2$CF$_3$ |
| 104 | bis-1,3-(2-perfluorohexylethyl)imidazolium | —CH$_2$CH$_2$— | (CF$_2$)$_5$CF$_3$ | —CH$_2$CH$_2$— | (CF$_2$)$_5$CF$_3$ |
| 105 | 1-(4,4,4-trifluorobutyl)-3-(3-perfluorohexylpropyl)imidazolium | —(CH$_2$)$_3$— | (CF$_2$)$_5$CF$_3$ | —(CH$_2$)$_3$— | CF$_3$ |
| 106 | bis-1,3-(3-perfluorooctylpropyl)imidazolium | —(CH$_2$)$_3$— | (CF$_2$)$_7$CF$_3$ | —(CH$_2$)$_3$— | (CF$_2$)$_7$CF$_3$ |
| 107 | 1-(5-perfluorooctylpentyl)-3-(3-perfluorooctylpropyl)imidazolium | —(CH$_2$)$_3$— | (CF$_2$)$_7$CF$_3$ | —(CH$_2$)$_5$— | (CF$_2$)$_7$CF$_3$ |
| 108 | bis-1,3-(3-perfluorododecylpropyl)imidazolium | —(CH$_2$)$_3$— | (CF$_2$)$_{11}$CF$_3$ | —(CH$_2$)$_3$— | (CF$_2$)$_{11}$CF$_3$ |
| 109 | bis-1,3-(3-perfluorohexadecylpropyl)imidazolium | —(CH$_2$)$_3$— | (CF$_2$)$_{15}$CF$_3$ | —(CH$_2$)$_3$— | (CF$_2$)$_{15}$CF$_3$ |
| 110 | bis-1,3-(7,7,7-trifluoroheptyl)imidazolium | —(CH$_2$)$_6$— | CF$_3$ | —(CH$_2$)$_6$— | CF$_3$ |
| 111 | bis-1,3-(9,9,10,10,10-pentafluorodecyl)imidazolium | —(CH$_2$)$_8$— | CF$_2$CF$_3$ | —(CH$_2$)$_8$— | CF$_2$CF$_3$ |
| 112 | bis-1,3-(6-perfluorohexadecylhexyl)imidazolium | —(CH$_2$)$_6$— | (CF$_2$)$_{15}$CF$_3$ | —(CH$_2$)$_6$— | (CF$_2$)$_{15}$CF$_3$ |
| 113 | bis-1,3-(8-perfluorododecyloctyl)imidazolium | —(CH$_2$)$_8$— | (CF$_2$)$_{11}$CF$_3$ | —(CH$_2$)$_8$— | (CF$_2$)$_{11}$CF$_3$ |
| 114 | 1-(6-perfluorooctylhexyl)-3-methylimidazolium | —CH$_2$— | H | —(CH$_2$)$_6$— | (CF$_2$)$_7$CF$_3$ |
| 115 | 1-(3-perfluorooctylpropyl)-3-methylimidazolium | —CH$_2$— | H | —(CH$_2$)$_3$— | (CF$_2$)$_7$CF$_3$ |
| 116 | 1-(6-perfluorobutylhexyl)-3-methylimidazolium | —CH$_2$— | H | —(CH$_2$)$_6$— | (CF$_2$)$_3$CF$_3$ |
| 117 | 1-(3-perfluoropentadecylpropyl)-3-methylimidazolium | —CH$_2$— | H | —(CH$_2$)$_3$— | (CF$_2$)$_{14}$CF$_3$ |

TABLE 1-continued

Exemplary compounds of the invention

| No. | Name of Imidazolium Portion of Compound | $R^1$ | $R^2$ | $R^3$ | $R^4$ |
|-----|------------------------------------------|-------|-------|-------|-------|
| 118 | 1-(3-perfluorooctadecylpropyl)-3-methylimidazolium | —CH$_2$— | H | —(CH$_2$)$_3$— | (CF$_2$)$_{17}$CF$_3$ |
| 119 | 1-(6-perfluorohexadecylhexyl)-3-methylimidazolium | —CH$_2$— | H | —(CH$_2$)$_6$— | (CF$_2$)$_{15}$CF$_3$ |
| 120 | 1-(6-perfluorooctylhexyl)-3-vinylimidazolium | vinyl | H | —(CH$_2$)$_6$— | (CF$_2$)$_7$CF$_3$ |
| 121 | 1-(3-perfluorooctylpropyl)-3-vinylimidazolium | vinyl | H | —(CH$_2$)$_3$— | (CF$_2$)$_7$CF$_3$ |
| 123 | 1-(6-perfluorobutylhexyl)-3-vinylimidazolium | vinyl | H | —(CH$_2$)$_6$— | (CF$_2$)$_3$CF$_3$ |
| 124 | 1-(3-perfluoropentadecylpropyl)-3-vinylimidazolium | vinyl | H | —(CH$_2$)$_3$— | (CF$_2$)$_{14}$CF$_3$ |
| 125 | 1-(3-perfluorooctadecylpropyl)-3-vinylimidazolium | vinyl | H | —(CH$_2$)$_3$— | (CF$_2$)$_{17}$CF$_3$ |
| 126 | 1-(6-perfluorohexadecylhexyl)-3-vinylimidazolium | vinyl | H | —(CH$_2$)$_6$— | (CF$_2$)$_{15}$CF$_3$ |

The compounds according to formula (1) can be prepared by any of the synthetic methods known in the art. In a preferred embodiment, the ionic compounds are prepared by reacting an imidazole with a fluorohydrocarbon-containing halide. If a counteranion other than the halide is desired, the resulting imidazolium halide can be reacted with a suitable compound capable of replacing the halide with another counteranion. For example, the synthesis may be practiced as follows:

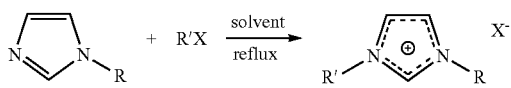

In the above reaction scheme, the R group may be H, a hydrocarbon group, or a fluoro-substituted hydrocarbon group and R' may be a hydrocarbon or fluoro-substituted hydrocarbon group such that the end product contains fluoro substitution. It is noteworthy that 1-methylimidazole (when R is methyl) and 1-vinylimidazole (when R is vinyl) are particularly available starting materials. The group X is typically a halide, but can be other anionic atoms or groups that cause the R' group to be sufficiently electrophilic for reacting with an amine group. The solvent is preferably a polar non-protic type of solvent such as acetonitrile.

In another aspect, the invention is directed to surface-functionalized particulate compositions. The particulate composition contains a particulate having adhered to its surface a fluoroionic compound of the general formula

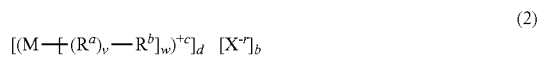

The particulate compositions are useful for several purposes. For example, they can be incorporated into polymer compositions, particularly fluoropolymer compositions, to increase the thermal conductance and/or structural properties of the polymeric material. They can also function as electrolyte materials, and under the proper conditions, as gas storage or microreaction vessel materials.

In formula (2), M represents a ring or ring system containing at least one nitrogen atom in the ring or ring system. One or more ring nitrogen atoms can be substituted aside from the —(R$^a$)$_v$—R$^b$ groups by any of the non-substituted or substituted hydrocarbon groups described above. Some examples of suitable nitrogen-containing rings include pyrrole, pyrrolidine, imidazole, 1-methylimidazole, pyrazole, piperidine, N-methylpiperidine, pyridine, piperazine, 1-methylpiperazine, 1-phenylpiperazine, pyrazine, pyrimidine, and triazine rings. Some examples of suitable nitrogen-containing ring systems include indole, purine, benzimidazole, 4-(pyridin-4-yl)pyridine, bipyridine, and 1,8-naphthyridine ring systems.

The group R$^a$ is a hydrocarbon linking group bound to a nitrogen atom of M and having at least one carbon atom, and optionally including one or more non-fluoro heteroatoms or heteroatom-containing groups. The subscript v appended to R$^a$ can assume a value of 0 or 1, thereby indicating whether R$^a$ is absent or present, respectively. When R$^a$ is not present, R$^b$ is directly attached to a nitrogen atom of M. All of the hydrocarbon linking groups already described above for R$^1$ and R$^3$ are applicable to R$^a$ (i.e., R$^a$ is aptly described by all of the hydrocarbon linking groups already described for R$^1$ and R$^3$).

The group R$^b$ is a fluoro-substituted hydrocarbon group having at least one carbon atom and at least one fluorine atom and optionally including one or more non-fluoro heteroatoms or heteroatom-containing groups. All of the fluoro-substituted hydrocarbon groups already described above for R$^2$ or R$^4$ are applicable to R$^b$ (i.e., R$^b$ is aptly described by all of the fluoro-substituted hydrocarbon groups already described for R$^2$ or R$^4$).

The subscript w is a positive integer representing the number of —(R$^a$)$_v$—R$^b$ units bound to an equal number of ring nitrogen atoms. More typically, w is a value of 1, 2, or 3. At least one of the ring nitrogen atoms to which a —(R$^a$)$_v$—R$^b$ unit is bound is positively charged.

The superscript +c represents a positive charge of magnitude c having a value of at least 1 and equal to the number of ring nitrogen atoms bound to —(R$^a$)$_v$—R$^b$ units. More typically, c is a value of 1, 2, or 3.

The group X$^{-r}$ represents an anion with negative charge –r, where r is a value of 1, 2, or 3. All of the applicable counteranions X have already been described above. In order to preserve charge neutrality, the subscripts b and d are integers such that c×d=b×r.

In a preferred embodiment, the ionic compounds of formula (2) are according to the ionic compounds of formula (1), i.e., wherein M is an imidazole ring containing either a hydrocarbon group, fluoro-substituted hydrocarbon group, or a combination thereof bound to one of its ring nitrogen atoms, and a (R$^a$)$_v$—R$^b$ group bound to the other nitrogen atom of imidazole (i.e., w is 1). All of the fluoroionic compounds already described above under formulas (1) and (3) are applicable to the surface-functionalized particulate compositions described above.

In the particulate composition, the particles can be of any suitable composition depending on the application. For example, when used for imparting a higher thermal conductance to a material, the particles are selected based on their thermal conductive properties. The particles can be composed of, for example, a metal or a main group element or compound. The metal compositions include, for example, all of the transition and rare earth metals. Some examples of metal compositions include copper, bronze, aluminum, and nickel. Other elements, such as barium and bismuth, can also be used as metals.

In one embodiment, the main group element or compound of the particles is non-carbon based. Some examples of such compositions include the Group III, V, and VII uncombined elements, as well as the oxide, sulfide, nitride, or phosphide compositions of these main group elements. Some examples of main group compositions include silicon oxide (conventional glass), aluminum oxide, gallium nitride, boronitride, indium phosphide, tin oxide, tin sulfide, lead oxide, aluminum phosphide, and zinc phosphide. Alkali and alkaline earth compositions can be suitable as well. These include, for example, magnesium oxide, calcium oxide, magnesium phosphide, calcium phosphide, lithium nitride, lithium oxide, and calcium sulfide. The particles can alternatively include ionic salt structures, such as, for example, the metal sulfates (e.g., calcium sulfate (gypsum)), metal hydroxides, metal phosphates, metal carbonates, clays, and minerals.

In a preferred embodiment, the particles of the particulate composition are carbon-based. By being carbon-based, the particles include carbon within their composition.

In one embodiment, the particles contain carbon combined with another one or more elements. Compositions containing carbon combined with one or more other elements include the hydrocarbons and the carbides (e.g., lithium carbide, calcium carbide, tungsten carbide, and aluminum carbide).

In another embodiment, the particles contain predominantly or solely carbon. All of the known allotropes of carbon are suitable for this embodiment. In a particular embodiment, the composition is a graphene-containing composition, i.e., carbon-based unsaturated compositions containing conjugated $sp^2$-hybridized carbon atoms engaged in carbon-carbon double bonds. Some examples of such carbon-based materials include fibers, nanofibers, graphite, fullerenes, carbon nanotubes, carbon nanobuds, carbon nanohorns, and their combined forms. The graphene-containing particles can be of any suitable shape, including open or enclosed. Open carbon-based particles can be, for example, curved, flat, or twisted. Some examples of enclosed carbon-based particles include carbon nanotubes and fullerenes.

In a preferred embodiment, the particles are carbon nanotubes. As known in the art, carbon nanotubes are enclosed and tubular in shape. They are typically only a few nanometers in diameter (e.g., 1-20 nm) and can have variable lengths of anywhere between nanometers to millimeters. The carbon nanotube can be any of the types of carbon nanotubes known in the art, including, for example, a single-walled carbon nanotube (SWNT or SWCNT), double-walled carbon nanotube (DWNT or DWCNT), or multiwalled carbon nanotube (MWNT or MWCNT). A single-walled carbon nanotube can have any suitable conformation, such as, for example, a zig zag mode (where m=0 of a n,m chiral vector), armchair mode (n=m), or chiral mode (all other chiral vector combinations). The synthesis of carbon nanotubes is well known in the art, and includes such methods as arc discharge, laser ablation, and chemical vapor deposition (CVD).

The particles can be of any suitable size. For most applications, it is preferable for the particles to be not more than micron-sized. Particularly when applying the particles as fillers for polymeric materials, it is preferable for the particles to be not more than 1 micron in any dimension. For example, the particles can have a size range of about 1 nm to 1 micron. In some embodiments, it may be preferable to further limit the size to no more than 500 nanometers (nm) or 250 nm in any dimension. For example, the particles can have a size range in any dimension of about 1 nm to 500 nm or 1 nm to 250 nm. In other embodiments, it may be preferable for the particles to be of nanoscale dimension (nanoscopic), i.e., a dimension sufficiently small that the properties of an object of such dimensions are predominantly governed by the behavior of individual atoms. Typically, a nanoscopic or nanoscale object refers to an object having at least one dimension within a range of about 1 to 100 nm.

The particles of the particulate composition are surface-functionalized by having the fluoroionic compounds described above being adhered onto their surfaces. The ionic compounds are typically adhered by some form of electrostatic interaction. The electrostatic interaction can include, for example, a π-π interaction between the positively charged group of the ionic compound and carbon-carbon double bonds of a graphene lattice.

Any of the methods known in the art used in surface functionalization of particles can be applied herein. For example in a preferred embodiment, the surface-functionalized particles are prepared by combining the ionic compound and the particles, preferably with application of heat (as in melt mixing), and then cooling and optionally grinding the cooled product into a powder.

In another aspect, the invention is directed to a fluorocomposite material containing a fluoropolymer having incorporated therein any of the surface-functionalized particulate compositions described above. The fluoroionic functionalization of the particles renders the particles more compatible, and thus, more dispersible and integratable with a fluoropolymer. The particles, by virtue of their composition, can impart beneficial properties to the fluoropolymer. Of primary relevance for the purposes of this invention is an increased thermal conductivity. However, the functionalized particles can also impart an increased mechanical strength, electrical conductivity, antistatic property, elasticity, and/or wear resistance.

Preferably, when the ionic liquids are used in the fluorocomposite materials, they have a decomposition temperature that is higher than the processing temperature of the fluoropolymer. The ionic liquids should also have high enough temperature stability to withstand an extrusion process. For example, it may be preferable to use ionic liquids with decomposition temperatures of at least, or above, 260° C. It is also preferable, where carbon nanoparticles, particularly carbon nanotubes, are used, that the ionic liquid have the ability to interact associatively with the surface of the carbon nanoparticle or carbon nanotube. A preferred associative interaction is one which includes π-π interactions between the electron-deficient cationic ring (e.g., imidazolium or pyridinium ring) of the ionic liquid and the conjugated graphite surface of a carbon nanoparticle or nanotube. In addition, it is preferable that the ionic liquids contain sufficient fluorine atoms so that they are able to effectively disperse into the fluoropolymer matrix.

The fluoropolymer can be any of the fluoropolymers known in the art. A fluoropolymer is any polymer containing fluorine atoms. The most predominant are the fluoropolymers derived by addition polymerization of fluoro-containing vinylic monomers. For example, the fluoropolymers can result from the addition polymerization of one or more monomer compositions described by the following formula:

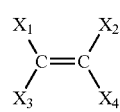
(4)

In formula (4), $X_1$, $X_2$, $X_3$, and $X_4$, can be, independently within a monomer and/or between different monomers represented by (4), a hydrogen atom, a fluorine atom, a chlorine atom, a group R representing a hydrocarbon group or a fluoro-substituted hydrocarbon group, or OR, wherein optionally, the hydrocarbon group or fluoro-substituted hydrocarbon group R includes one or more heteroatoms or heteroatom-containing groups, provided that at least one monomer of formula (4) in the final addition polymer contain at least one fluorine atom. The terms "hydrocarbon group," "fluoro-substituted hydrocarbon group," "heteroatoms," and "heteroatom-containing groups" are as defined above in the description provided for $R^2$ and $R^4$.

The polymer resulting from one or more monomers of formula (4) can be a homopolymer (i.e., containing only one type of formula (4) monomer), a copolymer (i.e., containing two distinct types of formula (4) monomers), a terpolymer (i.e., containing three distinct types of formula (4) monomers), or a higher multipolymer (i.e., containing more than three distinct types of formula (4) monomers). As the groups of formula (4) have been defined, either all monomers of the resulting polymer are fluoro-substituted, or some of the monomers are fluoro-substituted while others are not fluoro-substituted. Accordingly, copolymers, terpolymers, and higher multipolymers derived from monomers of formula (4) can contain non-fluorosubstituted monomer units, such as, for example, ethylene (—$CH_2CH_2$—), propylene (—CH($CH_3$)$CH_2$—), chloroethylenes (e.g., —CHClCH$_2$— or —CHClCHCl—), alkoxy-substituted ethylene (—CH(OR)CH$_2$—), methacrylic or methacrylate (e.g., —CH$_2$CH(C(O)OR)—), methylmethacrylic or methylmethacrylate (e.g., —CH$_2$CH(CH$_3$)(C(O)OR)—), vinylacetate, (e.g., —CH$_2$CH(OC(O)R)—), where R is H or a non-fluoro substituted or completely unsubstituted hydrocarbon as already defined above.

A copolymer, terpolymer, or higher multipolymer of the fluoropolymers can have any of the forms known in the art, including having an alternating, block, graft, or random arrangement of the monomer units. The invention also includes that monomer units can be linked by other than C—C bonds, such as, for example, ether (—C—O—C—), sulfur-containing (e.g., sulfonyl (—S(O)$_2$—) or —S—), nitrogen-containing (e.g., —NH—, —N(CH$_3$)— or —N=), and other heteroatom-containing bonds. The fluoropolymers can also include heteroatom groups (e.g., pendant groups) that are not linking.

More typically, the fluoropolymer is formed by recurring units according to the formula

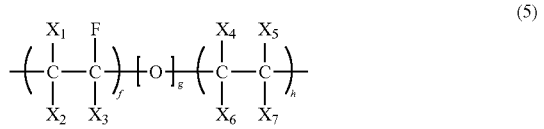

(5)

In formula (5), $X_1$, $X_2$, $X_3$, $X_4$, $X_5$, $X_6$, and $X_7$ can be, independently within a recurring unit and between recurring units, a hydrogen atom, a fluorine atom, chlorine atom, a group R representing a hydrocarbon group containing 1 to 6 carbon atoms or a fluoro-substituted hydrocarbon group containing 1 to 6 carbon atoms and at least one fluorine atom, or a group —OR. Some examples of more typical hydrocarbon groups include methyl, ethyl, n-propyl, and isopropyl. Some examples of more typical fluoro-substituted hydrocarbon groups include trifluoromethyl, perfluoroethyl, and perfluoropropyl. Some examples of more typical OR groups include methoxy, ethoxy, n-propoxy, isopropoxy, n-butoxy, isobutoxy, and t-butoxy.

In formula (5), the subscript f is a positive integer, and the subscript g is 0 or 1, depending on whether the linking oxygen atom is absent or present, respectively. The subscript h is 0 or a positive integer. In more common embodiments, g is 0, f is 1, and h is 0 or 1. The polymer can contain any number of recurring units of formula (4) or (5). Typically, the polymer will contain at least about 10, 20, or 30 recurring units and up to hundreds, thousands, or millions of recurring units.

Some examples of common fluoropolymers include fluorinated ethylene propylene (i.e., FEP, copolymer of tetrafluoroethylene (TFE) and hexafluoropropylene (HFP)), polytetrafluoroethylene (i.e., PTFE, homopolymer of TFE), the poly(perfluoroalkylvinylether)s (e.g., PFA and MFA), polyhexafluoropropylene (i.e., PHFP, homopolymer of HFP), polyhexafluoropropylene oxide (i.e., poly-HFPO or perfluoropolyether (PFPE) or perfluoroalkylether (PFAE) or perfluoropolyalkylether (PFPAE) having the general structure —(CF(CF$_3$)—CF$_2$—O)$_n$—), polychlorotrifluoroethylene (i.e., PCTFE, homopolymer of chlorotrifluoroethylene, CTFE), polyvinylidene fluoride (i.e., PVDF, homopolymer of vinylidene fluoride, VDF (CH$_2$=CF$_2$)), a copolymer of PVDF (e.g., PVDF-TrFE where TrFE is trifluoroethylene, or PVDF-HFP), polyvinylfluoride (i.e. PVF, homopolymer of vinylfluoride, VF), poly(ethylene-tetrafluoroethylene), i.e., PETFE copolymer (copolymer of ethylene and TFE), poly(ethylene-chlorotrifluoroethylene), i.e., PECTFE polymer (copolymer of ethylene and chlorotrifluoroethylene), THV (i.e., terpolymer of TFE, HFP, and VDF), and homopolymers or copolymers of perfluorobutylethylene (PFBE). These examples also include any of their copolymers, or mixtures thereof, or combinations thereof.

The poly(perfluoroalkylvinylether)s (or perfluoroalkoxy polymers) are, generally, fluoropolymers that include fluoro-substituted monomer units having one or more pendant alkoxy groups. More typically, these types of polymers contain at least one type of monomer unit of the type:

(6)

In formula (6) above, R represents a substituted or unsubstituted hydrocarbon group as already previously described. More typically, R is a straight-chained or branched unsubstituted hydrocarbon having 1 to 6 carbon atoms. Some examples of these types of fluoropolymers include PFA (a copolymer of perfluoropropylvinylether (PPVE) and TFE) and MFA (a copolymer of perfluoromethylvinylether (PPVE)).

Some trade name products of FEP include Neoflon™, Teflon®, Dyneon™, FluoroPlast™, and Dykor®. Some trade name products of PTFE include Fluon®, Algoflon®, Daikin-Polyflon™, Teflon®, Dyneon™, Heroflon™, and FluoroPlast™. Some trade name products of poly-HFPO include Krytox®. Some trade name products of PCTFE include Neoflon™. Some trade name products of PVDF include Hylar®, Hylar 5000®, Kynar®, Kynar 500®, Kynar Flex®, Solef PVDF®, and Dykor®. Some trade name products of PVF include Tedlar®. Some trade name products of PETFE include Aflon®, Neoflon™, Tefzel®, and Dyneon™. Some trade name products of PECTFE include Halar®.

The fluoropolymer composites can be prepared by any methods known in the art wherein the particulate can be integrally mixed or blended with the fluoropolymer. Typically, the fluoropolymer is a thermoplastic, thus requiring that it be melted before or during a combining step with the surface-functionalized particulate. The melted fluoropolymer having the surface-functionalized particulate incorporated therein is typically then casted by cooling, thereby forming the fluoropolymer composite of the invention. However, the fluoropolymer need not be a thermoplastic solid at ambient temperature, and hence, may not require a melting step for incorporating the surface-functionalized particulate. For example, the fluoropolymer can be in a sufficiently liquid state at ambient temperature to permit mixing or blending of the particulate. The liquid fluoropolymer may be intended to remain in the liquid state or may be processed further to be casted, by, for example, heating. The final solid fluoropolymer can be a thermoplastic or thermoset.

In a further embodiment, the fluoropolymer composite contains crosslinked bonds. The crosslinked bonds can be between the fluoropolymer and particulate, or between fluoropolymer regions, or between particulates, or any combination thereof. The crosslinked bonds can be a result of crosslinking between any crosslinkable groups residing on either the particulate, the fluoropolymer, or both. The crosslinked bonds can be, for example, hydrocarbon linking groups resulting from crosslinking of carbon-carbon double bonds (e.g., vinylic groups). The crosslinking bonds can also include, for example, an amido group (e.g., by condensation of an amino group and carboxyl group), an ester group (e.g., by condensation of a hydroxyl group with an ester or carboxyl group), an ether group (e.g., by reaction of a glycidyl or other epoxy-containing group with a hydroxyl group, or by the condensation reaction of hydroxyl groups with an aldehyde group), a urea group (e.g., by reaction of an isocyanate group with an amino group), a carbamate group (e.g., by reaction of an isocyanate group with a hydroxyl group), an imido group (e.g., by reaction of an amino group with an aldehyde or ketone), or a diazene group (e.g., by reaction of a diazonium salt with a nucleophilic aromatic group, such as phenol, anisole, or aniline).

The invention is also directed to a method for incorporating crosslinking into a fluoropolymer composite material. The method includes reacting crosslinkable groups residing on the fluoropolymer and/or surface of the particles of the particulate composition when both the fluoropolymer and particulate composition are in a combined state during the reacting step.

In one embodiment, the crosslinkable groups are already present in the fluoropolymer and/or particles, thereby eliminating the need for a functionalization step before the crosslinking reaction. In another embodiment, the fluoropolymer and/or particles require functionalization with crosslinkable groups before the crosslinking reaction.

The fluoropolymer can be functionalized with crosslinkable groups by any suitable method known in the art. Some of these methods include the application of chemical grafting, radiation grafting, plasma grafting, ozonation grafting, and ultraviolet (UV) grafting.

In a preferred embodiment, the fluoropolymer is functionalized with crosslinkable groups by radiation grafting. For example, the fluoropolymer can be irradiated by use of high energy radiation and grafted with a compound containing carbon-carbon double bonds. A subclass of these compounds can be conveniently described according to formula (7) below.

$$R^c(CR_2)_nCH=CHR^d \qquad (7)$$

In formula (7) above, R can be a hydrogen atom, fluorine atom, or any of the hydrocarbon groups, as previously defined, particularly according to the description given for the groups represented by —$R^1$-$R^2$. More typically, R is H or F. The group $R^c$ is a crosslinkable functional group, such as, for example, an amino, vinyl, acyl chloride (e.g., acryloyl chloride), carboxyl, hydroxyl, glycidyl or isocyanate group. The group $R^d$ can be any of the groups as defined for R, but more preferably represents a hydrogen, methyl, ethyl, propyl, isopropyl, n-butyl, isobutyl, methoxy, ethoxy or propoxy group. More preferably, $R^d$ is a hydrogen atom. The subscript n can be any suitable value, preferably within the range of 1-20, more preferably 2-10, more preferably 3-10, and even more preferably 6-8. The compound according to formula (7) will insert into the polymer through its carbon double bonds, thereby exposing the $R^c$ group.

In a preferred embodiment, $R^c$ is an amino group or hydroxyl group and $R^d$ is a hydrogen atom. The amino group can be used to crosslink with amino-reactive groups (e.g., an acyl chloride, acryloyl chloride, carbonyl, carboxyl, ester, or isocyanate group) residing on the fluoropolymer or particles. The hydroxyl group can be used to crosslink with hydroxyl-reactive groups (e.g., an acyl chloride, acryloyl chloride, ester, carboxyl, or isocyanate group) residing on the fluoropolymer or particles. Alternatively, the amino or hydroxyl group can be further reacted with a chemical that will convert these groups, or link to these groups, to provide a different or modified reactive group. For example, the amino or hydroxyl group can be reacted with acryloyl chloride, thereby resulting in the conversion of these groups to a vinyl-capped group. The vinyl-capped group can then be crosslinked with, for example, other vinylic groups residing on either the fluoropolymer or particles.

The particles of the particulate composition can also be functionalized with crosslinkable groups by any suitable method known in the art. In one embodiment, the particles are functionalized with crosslinkable groups by surface-functionalizing with one or more ionic compounds (such as the fluoroionic compounds described above) that also contain a crosslinkable group. For example, the ionic compound can be a vinyl-containing compound, such as the vinyl-containing ionic compounds 55-63 or 120-126 shown in Table 1. The vinyl groups on the particles can be made to crosslink with each other or with vinyl groups on the fluoropolymer, if present. In another embodiment, particles can be functionalized by chemically attaching to the particles (e.g., by covalent bond attachment) groups containing crosslinkable portions therein. For example, it may be desirable for the particles to be covalently functionalized with crosslinkable groups and additionally functionalized with fluoroionic compounds. In this manner, the particles are capable of being crosslinked either with themselves or the fluoropolymer while also being readily dispersible within the fluoropolymer before crosslinking. It is also possible for a covalently-attached crosslinkable group to contain a fluoroionic component.

In one embodiment, the crosslinking occurs between fluoropolymer crosslinkable and particulate crosslinkable groups. In another embodiment, the crosslinking occurs between fluoropolymer crosslinkable groups. In yet another embodiment, the crosslinking occurs between particulate crosslinkable groups. In still another embodiment, the crosslinking occurs by a combination of the foregoing crosslinking embodiments. For example, in one embodiment the crosslinking may occur between fluoropolymer segments and between fluoropolymer and particulate, but not between particulate, whereas in another embodiment the crosslinking may occur between fluoropolymer segments, and between particulate, and between fluoropolymer and particulate.

Any method known in the art for inducing crosslinking can be used herein. In one embodiment, crosslinking is induced by physical means. For example, in the case of crosslinking between vinylic groups, any of the suitable curing methods known in the art can be used. Some of these curing methods include application of ultraviolet (UV), high energy radiation, heat, plasma, or a combination thereof.

The opacity of carbon nanotubes may prevent radiation, such as UV, to completely penetrate into the fluoropolymer composite material. This would lead to incomplete curing. Accordingly, in order to ensure complete curing, it is more preferable to use a combined UV and heat curing process.

In another embodiment, crosslinking is induced by chemical means. The chemical means may be a one-step process. For example, a crosslinking reaction between an acyl chloride (e.g., acryloyl chloride) and amino or hydroxy crosslinkable groups can occur simply by contacting the crosslinkable groups under suitable conditions known in the art. Alternatively, the crosslinking reaction (e.g., between carboxylic and amino crosslinkable groups) may require chemical activation means, by use of a suitable activation group. Some activating groups particularly suitable for activating amines and alcohols include, for example, the class of carbodiimide compounds, such as DCC, DIC, and EDC. The chemical activation may also require the application of heat or radiation to promote the activation step.

In another embodiment, crosslinking can be induced between particles of the particulate composition when the particles are not combined with the fluoropolymer. The resulting crosslinked particulates can be useful in themselves according to the uses described above for the functionalized particulate composition described above. Alternatively, the crosslinked particulates can be incorporated into the fluoropolymer by any of the means described above. If desired, further crosslinking between fluoropolymer and particulate, or between fluoropolymer segments, can also be made to occur.

In another aspect, the invention is directed to an article of manufacture constructed, at least in part, by the fluoropolymer composite materials described above. The article, can be, for example, a printing roller, tube, hose, sheet, fitted cover, protective cover, sleeve, film, block, ring, ball, part of an electrical component, or part of a medical device.

Examples have been set forth below for the purpose of illustration and to describe the best mode of the invention at the present time. However, the scope of this invention is not to be in any way limited by the examples set forth herein.

EXAMPLE 1

Syntheses of Ionic Liquids

The reagents 3-(perfluorooctyl)propylamine, 3-(perfluorooctyl)propyl iodide, 1-methylimidazole, 1-vinylimidazole, hexafluorophosphoric acid (60% water solution), and other reagents were obtained from Sigma-Aldrich Co. The ionic liquids IL-1 and IL-2 were synthesized using the general scheme shown in FIG. 1.

1. Synthesis of 1-(3-perfluorooctylpropyl)-3-methylimidazolium hexafluorophosphate (IL-1) ionic liquid Typically, 0.7 g (8.5 mmol) of 1-methylimidazole and 5.0 g (8.5 mmol) of 3-(perfluorooctyl)propyl iodide were dissolved into 20 mL of acetonitrile. The mixture was refluxed at 85° C. for 24 hours, and subsequently cooled down to room temperature. The resulting samples were filtered and washed with ethyl ether three times. The 1-(3-perfluorooctyl)propyl-3-methylimidazolium iodide was obtained as a white powder after being dried in a vacuum oven. The yield from this reaction was about 90%.

Then 2.5 g (3.7 mmol) of 1-(3-perfluorooctyl)propyl-3-methylimidazolium iodide was dispersed into 100 mL of water. To this, 0.7 mL (5.0 mmol) of hexafluorophosphoric acid aqueous solution was slowly dropped into the suspension under continuous stirring. The mixture was stirred for 24 hours at room temperature. Methylene chloride was subsequently added to form a two-layer mixture, allowing the removal of the water layer. After evaporation, the white solid was washed with water until neutral. The powdery product was dried in a vacuum oven. The yield of this procedure was about 95%.

2. Synthesis of 1-(3-perfluorooctyl)propyl-3-vinylimidazolium hexafluorophosphate (IL-2) ionic liquid An analogous procedure was followed to the synthesis above, except that 1-vinylimidazole was used instead of 1-methylimidazole. The final yield of this product was about 80%.

EXAMPLE 2

Physical Modification of MWCNT with Ionic Liquids (Formation of iMWCNT)

Figure 2:
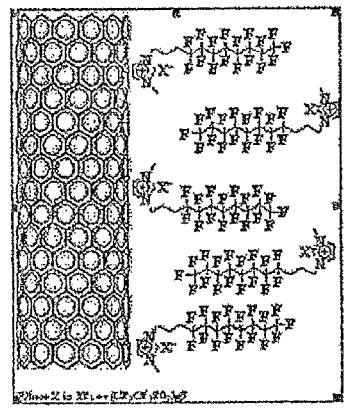
FIG. 2. A schematic representation of π-stacking arrangement of ionic liquids on a multiwalled carbon nanotube (MWCNT) surface functionalized with ionic liquids, also known as an iMWCNT.

A proportional mixture of IL-1 or IL-2 and oxidized MWCNT was melt mixed using a twin-screw blender (DACA instruments) at 300 r/min for 2 min. After cooling, the blend yielded a solid material that was ground into a powder before using. A schematic representation of the π-stacking arrangement of ionic liquids on an MWCNT surface functionalized with ionic liquids is shown in FIG. 2.

EXAMPLE 3

Preparation of Nanocomposite Film Based on iMWCNT and FEP

Figure 3:
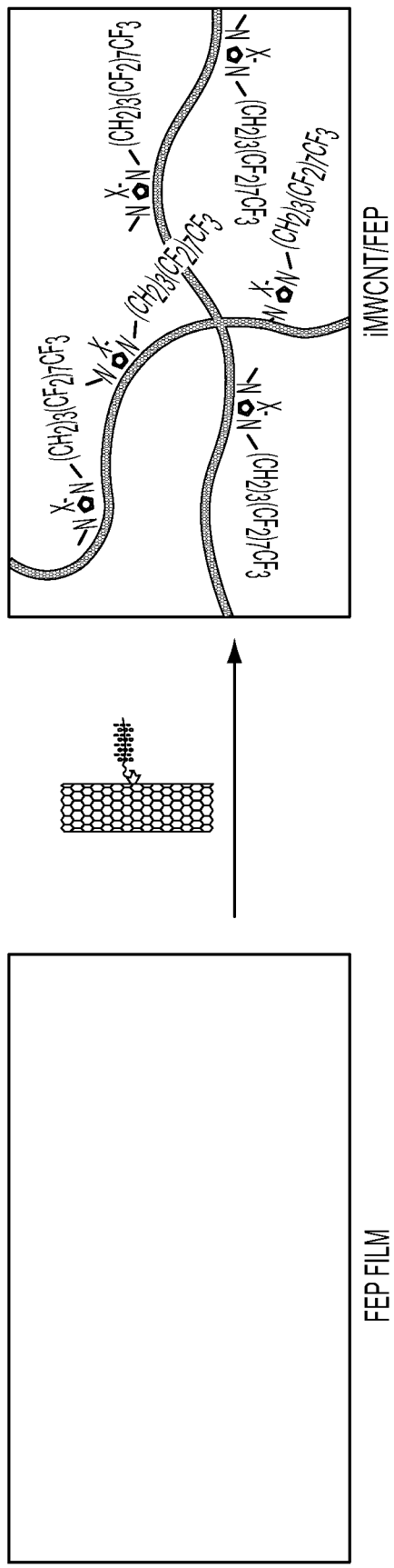
FIG. 3 A schematic representation of a preferred method for the preparation of a nanocomposite formed by incorporating an ionic liquid-functionalized carbon nanotube (iMWCNT) in a fluoropolymer matrix (FEP). The resulting nanocomposite is referred to as an iMWCNT/FEP nanocomposite.

The iMWCNT (modified by IL-1) was mixed with FEP powders using a twin-screw blender at 270° C. for 5-20 min. All samples were melt-pressed at 270° C. into films with a thickness of about 0.1-0.5 mm. The composition of the nanocomposites is listed in Table 2 below. The preparation of iMWCNT/FEP nanocomposite is shown schematically in FIG. 3.

TABLE 2

| Nanocomposites of iMWCNT/FEP | |
| --- | --- |
| Nanocomposites | Composition (weight ratio) |
| 1 | FEP:MWCNT:IL-1 = 100:0.5:0.5 |
| 2 | FEP:MWCNT:IL-1 = 100:0.5:5.0 |

EXAMPLE 4

Chemical Grafting of a MWCNT for Introducing Crosslinkable Groups (Formation of gMWCNT)

The multiwall carbon nanotube (MWCNT) material was purchased from Nanostructured and Amorphous Materials, Inc. The diameter of the MWCNT was about 8-15 nm. The as-received MWCNT sample was oxidized with concentrated $H_2SO_4/HNO_3$ mixture (3:1) at 30° C. for 3 hours under microwave. The oxidized MWCNT was separated by washing with water, methanol (several times), and drying at 80° C. for 24 hours under vacuum after filtration. The oxidized MWCNT was refluxed in thionyl chloride for 24 hours at 65° C., and then the thionyl chloride was removed by distillation.

Figure 4:
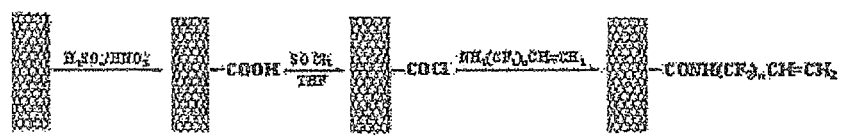
FIG. 4 A schematic representation of a preferred method for the preparation of acyl chloride-functionalized MWCNT and its reaction with an aminoalkenyl compound to form a chemical-grafted MWCNT (i.e., a gMWCNT) having an exposed vinyl group.

The resulting dried acyl chloride-functionalized MWCNT can be combined with a fluoropolymer functionalized with crosslinkable groups reactive to an acyl chloride (e.g., an amino group). Alternatively, the acyl chloride-functionalized MWCNT can be further reacted with, for example, an amino-substituted vinylic compound to produce a vinyl-functionalized MWCNT. The vinyl-functionalized MWCNT may be crosslinked with itself, or alternatively, or in combination, crosslinked with a fluoropolymer that has been functionalized with vinylic groups, or other groups capable of crosslinking with the vinyl groups on the MWCNTs. FIG. 4 shows one possible synthetic method for producing the acyl chloride MWCNT and functionalizing the MWCNT with a vinyl-capped amine to produce a MWCNT with vinyl crosslinkable groups.

Figure 5:
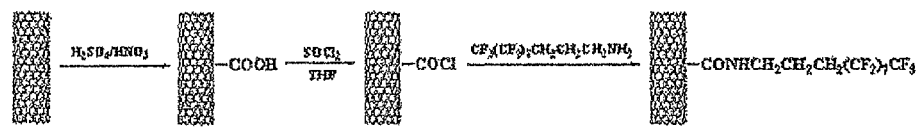
FIG. 5 A schematic representation of a preferred method for the preparation of a fluorinated carbon nanotube by chemical reaction of an acyl chloride-functionalized MWCNT with an amino-functionalized fluoro-substituted compound.

The dried acyl chloride MWCNT can also be reacted with a suitable end-functionalized fluoro-substituted compound to additionally functionalize the carbon nanotube. For example, the dried acyl chloride MWCNT was reacted with 3-perfluorooctylpropylamine in dry THF using TEA as a catalyst at 75° C. for two days. The chemical-grafted MWCNT (gMWCNT) was obtained by washing with water and THF and drying in vacuum at 70° C. One possible synthetic route for producing such a chemical-grafted MWCNT is shown in FIG. 5.

EXAMPLE 5

Chemical Modification and Functionalization of Fluoropolymers for Introducing Crosslinkable Groups Fluoro-ethylene-propylene copolymer (Teflon FEP100) was purchased from DuPont, USA. FEP films were cut into pieces, packed, and sealed and irradiated on an aluminum tray by high energy radiation (e.g., irradiated by an electron accelerator under air atmosphere and at room temperature where mean electron energy was about 1 MeV and the energy doses about 50 kGy). Immediately after the treatment, the films were cooled to –30° C. and stored for further use. The grafting reaction was carried out in glass ampoules under nitrogen atmosphere.

Figure 6:
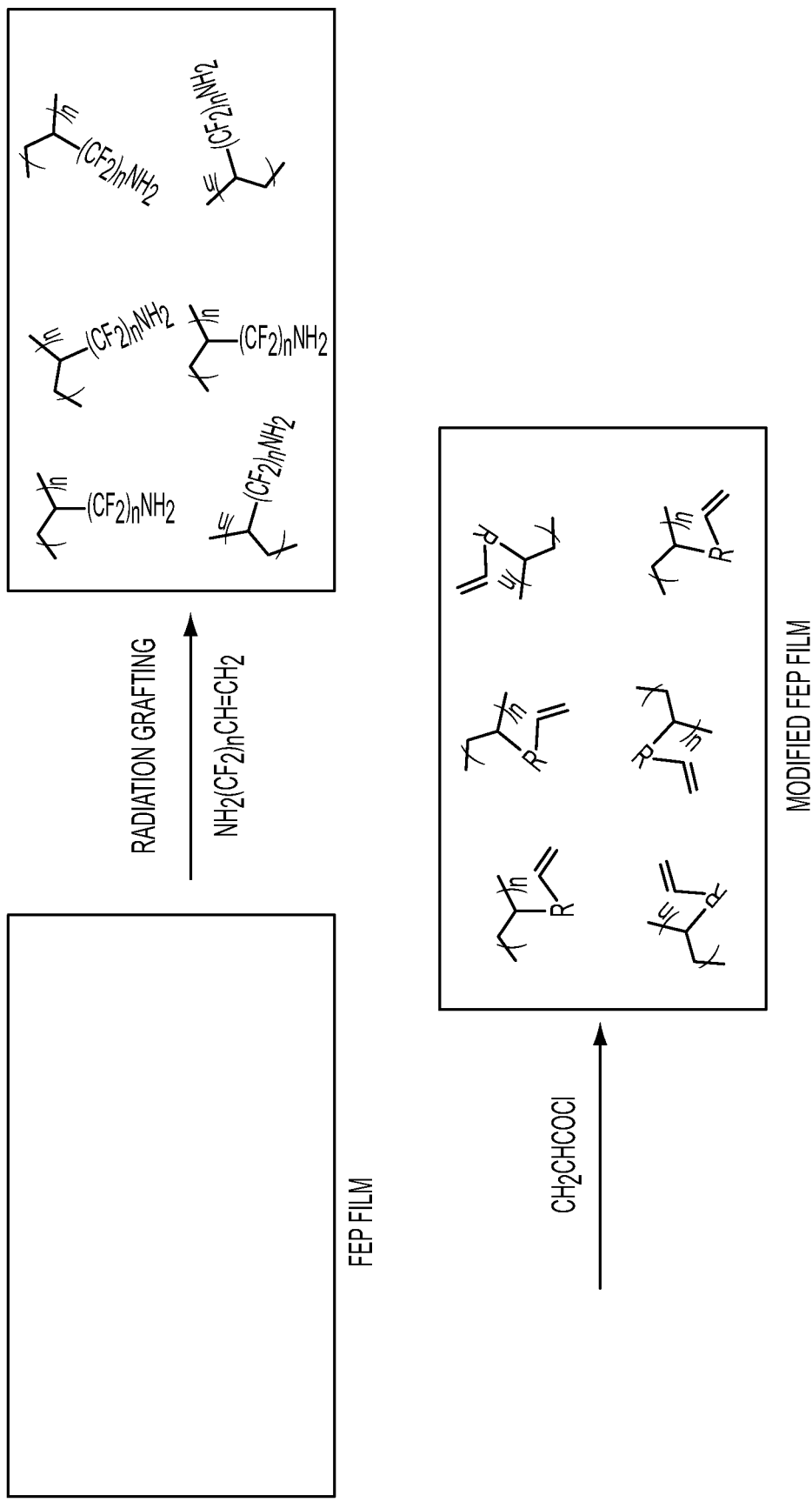
FIG. 6 A schematic representation showing a preferred method for surface modification and functionalization of a fluoropolymer by radiation grafting using an amino-vinyl grafting compound of the formula $NH_2(CF_2)_nCH=CH_2$.

1. The exposed samples were placed in reaction tubes containing a fluoroalkenylamine (for example, a compound of general formula $H_2N(CF_2)_n$—CH=$CH_2$, where n is any suitable integer, but particularly where n=6 to 8), water, and ferrous sulfate as homopolymer initiator. Nitrogen was bubbled through the solution to remove air from the tube. The tubes were subsequently placed in a constant temperature water bath at 50° C. for a suitable period of time dependent on the thickness of the film, intensity of radiation, and other factors. The grafting time was typically about 1 to 10 minutes, and more typically 1 to 5 minutes. After the grafting reaction, the samples were washed, purified, and dried under vacuum to a constant weight. The dried irradiated FEP film was then reacted with acryloyl chloride in an ice bath. The radiation-grafted FEP film was obtained by washing with water and drying under vacuum at room temperature. The method is shown schematically in FIG. 6.

Figure 7:
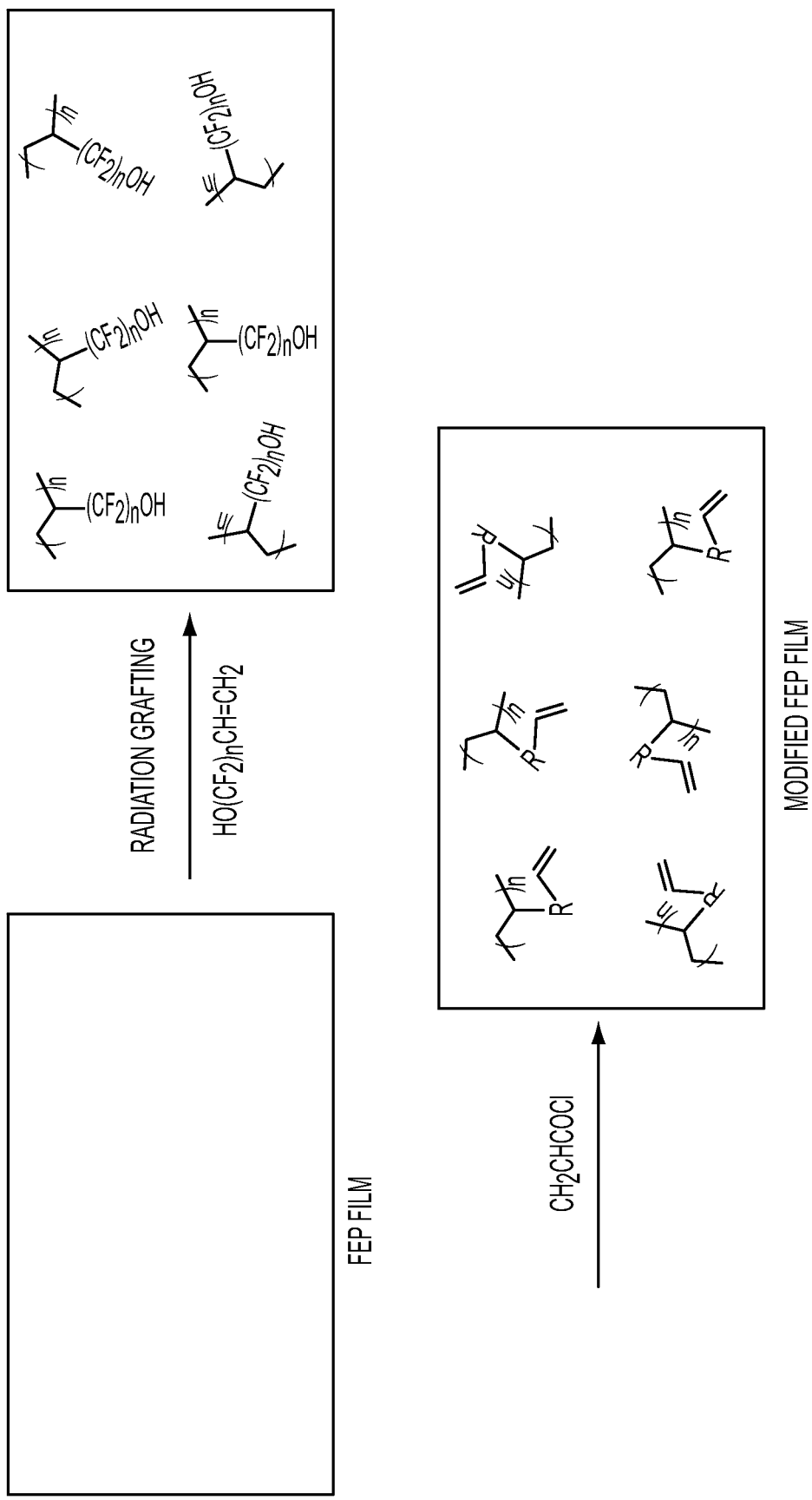
FIG. 7 A schematic representation showing a preferred method for surface modification and functionalization of a fluoropolymer by radiation grafting using a hydroxyl-vinyl grafting compound of the formula $HO(CF_2)_nCH=CH_2$.

2. The exposed samples were placed in reaction tubes containing a fluoroalkenylalcohol (for example, a compound of general formula $HO(CF_2)$—CH=$CH_2$, where n is any suitable integer, but particularly where n=6 to 8), water, and ferrous sulfate as homopolymer initiator. Nitrogen was bubbled through the solution to remove air from the tube. The tubes were subsequently placed in a constant temperature water bath at 50° C. for a suitable period of time dependent on the thickness of the film, intensity of radiation, and other factors. The grafting time was typically about 1 to 10 minutes, and more typically 1 to 5 minutes. After the grafting reaction, the samples were washed, purified, and dried under vacuum to a constant weight. The dried irradiated FEP film was then reacted with acryloyl chloride in an ice bath. The radiation-grafted FEP film was obtained by washing with water and drying under vacuum at room temperature. The method is shown schematically in FIG. 7.

EXAMPLE 6

Preparation of Elastomeric Fluoropolymer Nanocomposites Based on gMWCNT

An as-received oxidized MWCNT prepared by $H_2SO_4/HNO_3$ was refluxed with $SOCl_2$ to produce an acyl chloride-functionalized MWCNT. This was then reacted with a fluoroalkenylamine, as described in Example 4 and FIG. 4. The final modified MWCNT contained vinyl groups, and could therefore, be crosslinked in the presence of initiators by application of heat and UV after being melt-dispersed into the fluoropolymer matrix.

Figure 8:
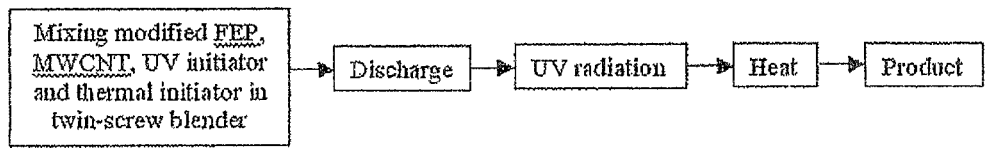
FIG. 8 Process flow chart showing a preferred method for the preparation of a crosslinked nanocomposite by a dual cross-linking system using UV and thermal curing.
Figure 9:
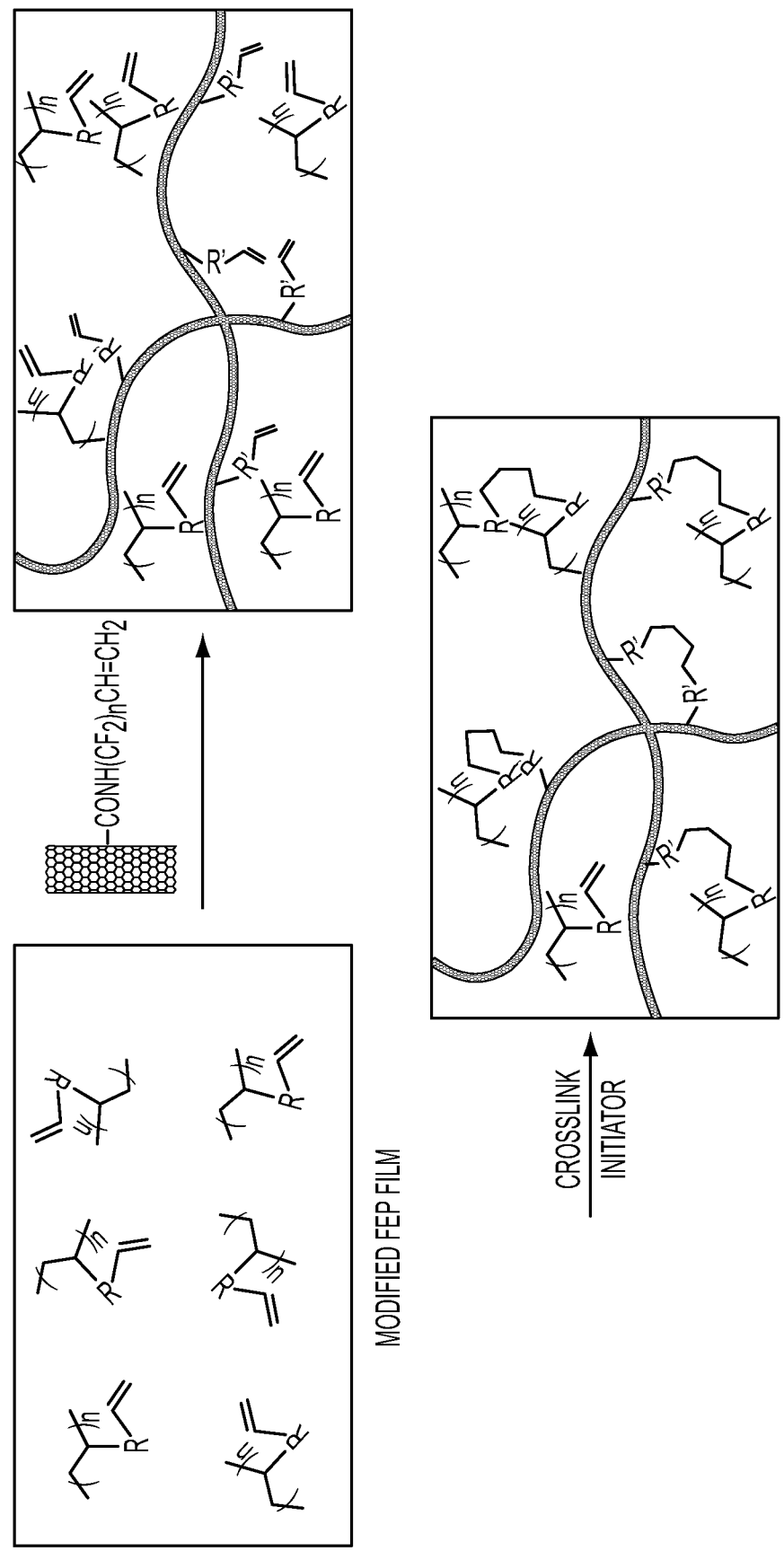
FIG. 9 A schematic representation showing a preferred method for the preparation of a crosslinked fluoropolymer nanocomposite by crosslinking vinyl groups in the fluoropolymer and carbon nanotubes by use of a dual UV-thermal curing process.

Fluoropolymer nanocomposite elastomer was prepared by a dual cross-linking system with UV and thermal curing process. A proportional mixture of modified FEP, MWCNT, UV initiator and thermal initiator were melt mixed using a twin-screw blender (DACA instruments) at 100° C. for 20 min. Then the mixture was cured by UV radiation for 5 min and heat treated at 280° C. for another 10 min. A preferred physical process for accomplishing this is shown in the process flow chart of FIG. 8. At least one possible chemical process by which the crosslinking occurs is shown in FIG. 9. The patterned lines in FIG. 9 represent associated MWCNTs that have been functionalized with end-vinyl groups (as described in Example 4 and FIG. 4) and blended into a vinyl-functionalized FEP film (as described in Example 5 and FIGS. 6 and 7).

EXAMPLE 7

Preparation of Elastomeric Fluoropolymer Nanocomposites Based on iMWCNT

Figure 10:
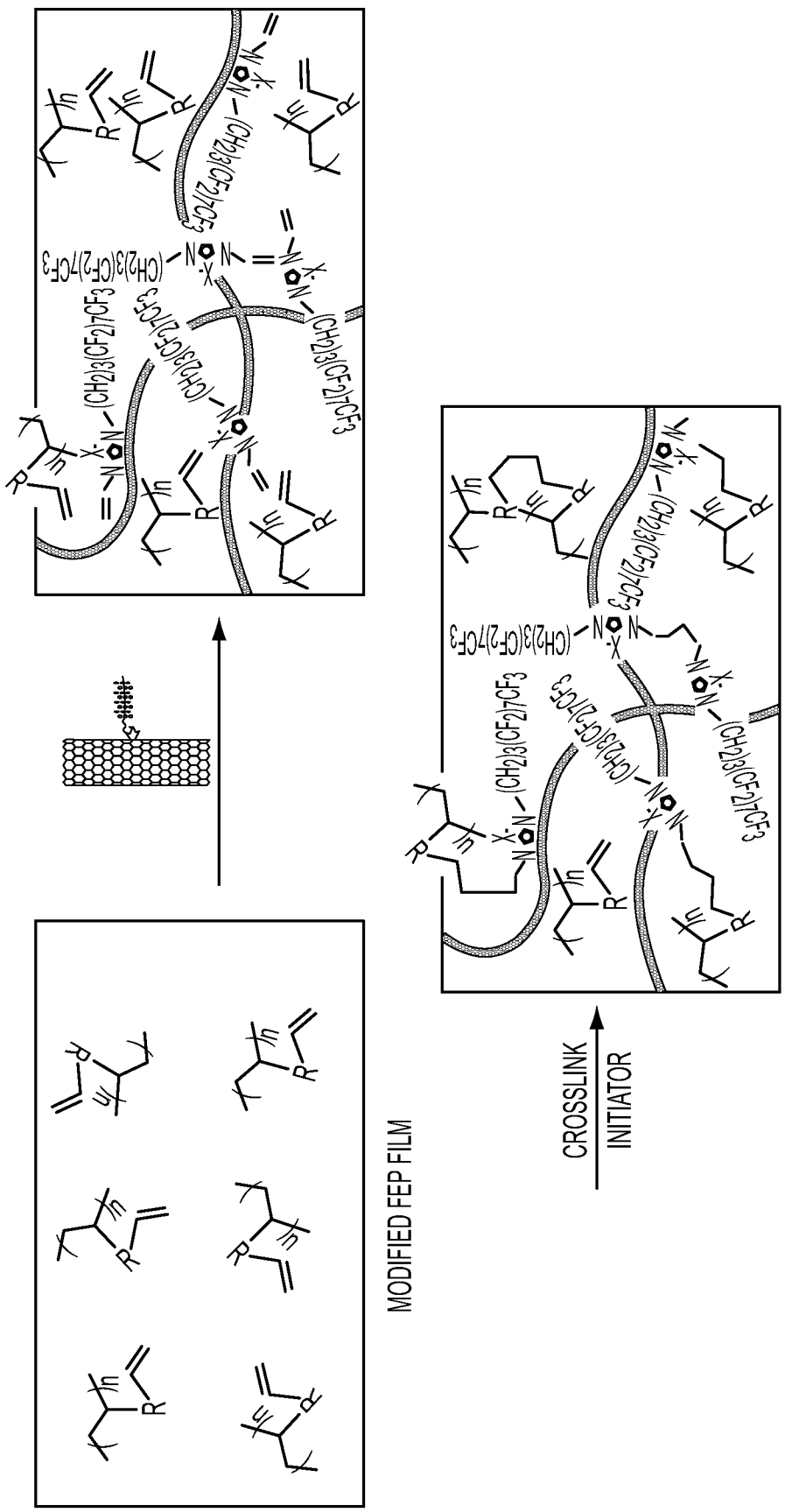
FIG. 10 A schematic representation showing a preferred method for the preparation of a fluoropolymer nanocomposite elastomer containing vinyl-functionalized iMWCNT by use of a dual UV-thermal curing process.

The iMWCNT modified by IL-2 (the vinyl-containing fluoroionic liquid described in Example 1 and FIG. 1) was mixed with modified FEP particles and initiator using a twin-screw blender at 270° C. for 5-20 minutes. The vinyl group in IL-2 was polymerized at this condition and a crosslinked MWCNT framework was formed. This crosslinking improved the elastomeric properties of this nanocomposite. The composition of the elastomeric nanocomposites is listed in Table 3 below. One possible method for producing an elastomeric fluoropolymer nanocomposite is shown in FIG. 10.

TABLE 3

Nanocomposite Elastomers of iMWCNT/FEP

| Nanocomposites | Composition (weight ratio) |
|---|---|
| 3 | FEP:MWCNT:IL-2:initiator = 100:0.5:0.5:0.5 |
| 4 | FEP:MWCNT:IL-2:initiator = 100:0.2:2.0:0.5 |

EXAMPLE 8

Preparation of Elastomeric Fluoropolymer Nanocomposites by Chemical Crosslinking Another way to produce the fluoropolymer elastomer in accordance with the present invention is by chemical crosslinking of reactive crosslinkable groups. In a preferred embodiment, the crosslinking was accomplished by crosslinking two kinds of modified carbon nanotubes (preferably MWCNTs) with different functional groups. The two types of carbon nanotubes were dispersed into modified FEP by melting extrusion, and then crosslinked by chemical reaction of the crosslinkable groups. The crosslinking step resulted in the formation of a crosslinked framework of modified MWCNT in the FEP matrix. The resulting nanocomposite displayed an improved elastomeric property.

Figure 11:
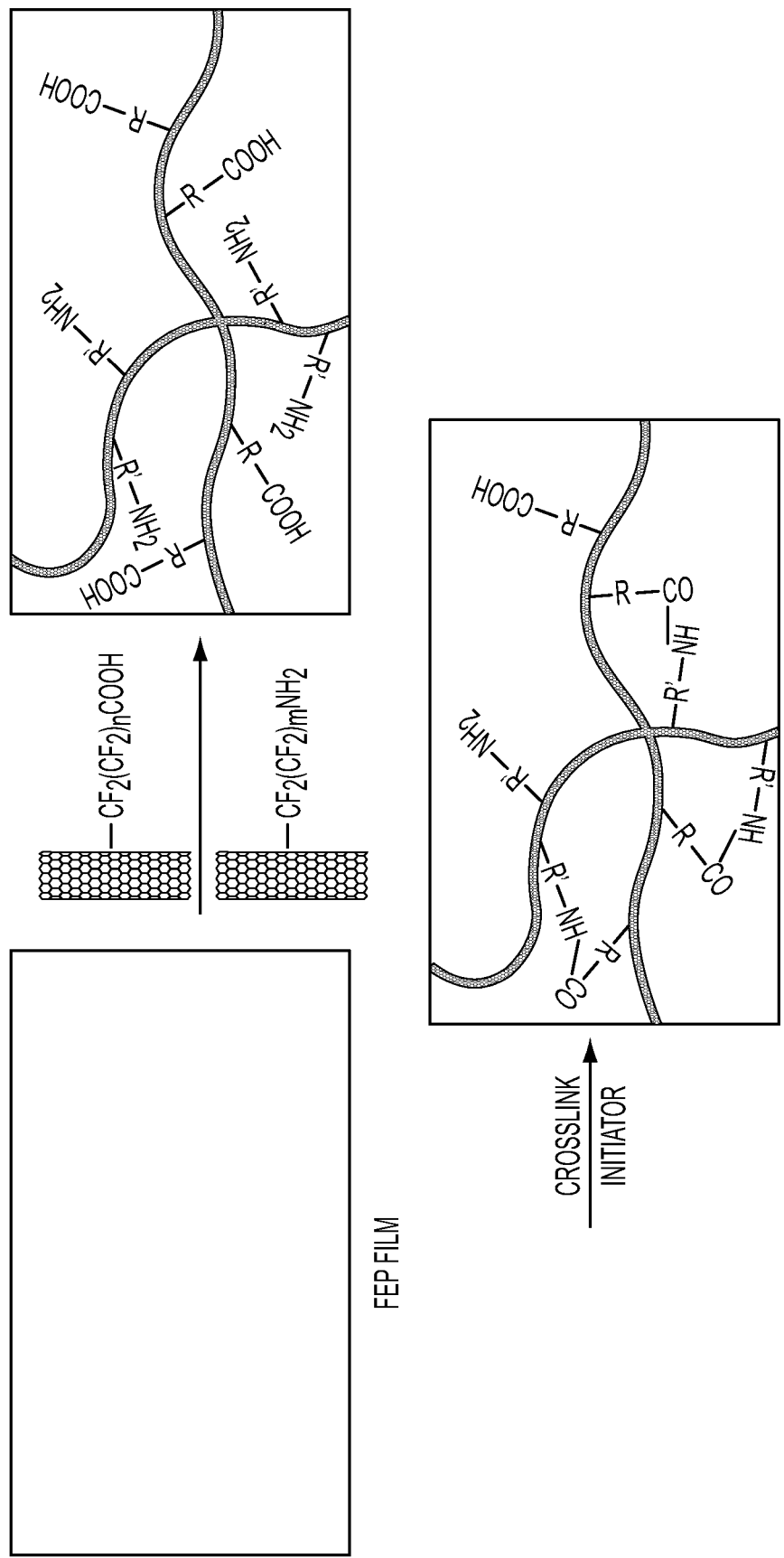
FIG. 11 A schematic representation showing a preferred method for the preparation of a crosslinked fluoropolymer nanocomposite by a method wherein carboxyl-functionalized and amino-functionalized carbon nanotubes are chemically crosslinked to form amide crosslinking bonds.
Figure 12:
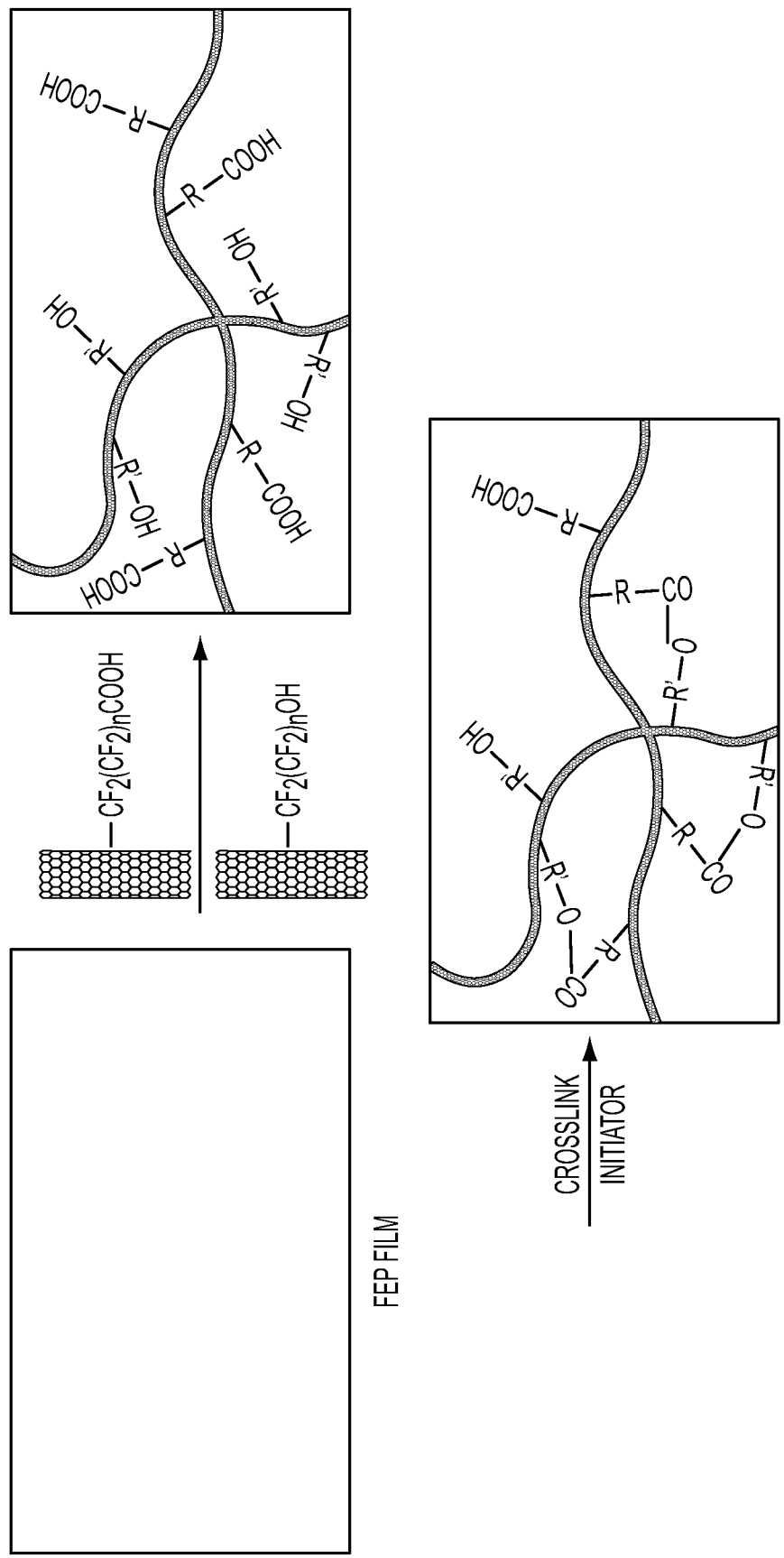
FIG. 12 A schematic representation showing a preferred method for the preparation of a crosslinked fluoropolymer nanocomposite by a method wherein carboxyl-functionalized and hydroxyl-functionalized carbon nanotubes are chemically crosslinked to form ester crosslinking bonds.

For example, FIG. 11 shows one possible method of chemical crosslinking by crosslinking carbon nanotubes separately functionalized with carboxylic acid and amino groups. From this reaction, amide crosslinking bonds result. FIG. 12 shows another possible method of chemical crosslinking by crosslinking carbon nanotubes separately functionalized with carboxylic acid and hydroxyl groups. From this reaction, ester crosslinking bonds result.

It is important to note that crosslinking can also be made to occur by use of any other suitable combinations of reactive groups, as described above, e.g., amino and ester, hydroxyl and ester, isocyanato and hydroxyl, amino and halide, hydroxyl and aldehyde or ketone, and so on.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A fluoropolymer composite material comprising a fluoropolymer having incorporated therein a surface-functionalized particulate composition comprising a particulate having adhered to its surface an ionic compound of the general formula

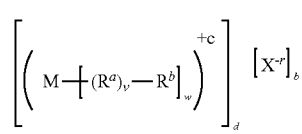

(2)

wherein M represents a ring or ring system containing at least one nitrogen atom in the ring or ring system;
$R^a$ is a hydrocarbon linking group bound to a nitrogen atom of M and having at least one carbon atom, and optionally including one or more non-fluoro heteroatoms or heteroatom-containing groups;

$R^b$ is a fluoro-substituted hydrocarbon group having at least one carbon atom and at least one fluorine atom and optionally including one or more non-fluoro heteroatoms or heteroatom-containing groups;
the subscript v is 0 or 1, where a value of 0 for a subscript represents the absence of a group to which the subscript is appended, and a value of 1 represents the presence of a group to which the subscript is appended;
the subscript w is a positive integer representing the number of —$(R^a)_v$—$R^b$ units bound to an equal number of ring nitrogen atoms;
+c represents a positive charge of magnitude c having a value of at least 1 and equal to the number of ring nitrogen atoms bound to —$(R^a)_v$—$R^b$;
$X^{-r}$ represents an anion with negative charge –r, where r is a value of 1, 2, or 3;
the subscripts b and d are integers such that c×d=b×r,
wherein the general formula 2 is according to the formula

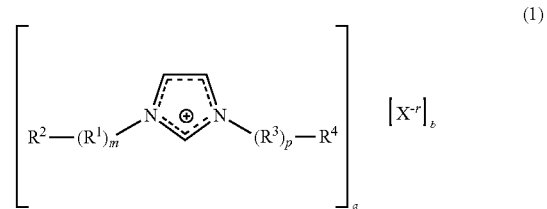

(1)

wherein:
$R^1$ and $R^3$ are, independently, hydrocarbon linking groups having at least one carbon atom, and optionally including one or more non-fluoro heteroatoms or heteroatom-containing groups;
$R^2$ is either a hydrogen atom, or a fluoro-substituted hydrocarbon group having at least one carbon atom and at least one fluorine atom and optionally including one or more non-fluoro heteroatoms or heteroatom-containing groups, or a heteroatom-containing group only when m is 1, wherein —$R^1$—$R^2$ represents a vinyl group;
$R^4$ is a fluoro-substituted hydrocarbon group having at least one carbon atom and at least one fluorine atom and optionally including one or more non-fluoro heteroatoms or heteroatom-containing groups;
the subscripts m and p are independently 0 or 1, where a value of 0 for a subscript represents the absence of a group to which the subscript is appended, and a value of 1 represents the presence of a group to which the subscript is appended;
$X^{-r}$ represents an anion with negative charge –r, where r is a value of 1, 2, or 3; and
the subscripts a and b are positive integers such that a=b× r' wherein m is 1.

2. The fluoropolymer composite material of claim 1, wherein the particulate has a composition comprising a metal.

3. The fluoropolymer composite material of claim 1, wherein the particulate has a composition comprising a non-carbon main group element.

4. The fluoropolymer composite material of claim 3, wherein the particulate has a composition comprising an oxide, sulfide, nitride, or phosphide material.

5. The fluoropolymer composite material of claim 4, wherein the particulate has a composition comprising glass.

6. The fluoropolymer composite material of claim 1, wherein the particulate has a composition comprising a carbon-based composition.

7. The fluoropolymer composite material of claim 6, wherein the carbon-based composition is a hydrocarbon composition.

8. The fluoropolymer composite material of claim 6, wherein the carbon-based composition is a graphene-containing composition.

9. The fluoropolymer composite material of claim 8, wherein the particulate is selected from graphene sheets, graphite nanoparticles, carbon nanotubes, fullerenes, carbon nanohorns, carbon nanobuds, and combinations thereof.

10. The fluoropolymer composite material of claim 1, wherein $R^2$ is a hydrogen atom.

11. The fluoropolymer composite material of claim 10, wherein $R^1$ is a hydrocarbon linking group having 1 to 6 carbon atoms and no heteroatoms.

12. The fluoropolymer composite material of claim 11, wherein p is 1.

13. The fluoropolymer composite material of claim 12, wherein $R^3$ is a hydrocarbon linking group having 1 to 6 carbon atoms.

14. The fluoropolymer composite material of claim 13, wherein $R^4$ is a fluoro-substituted hydrocarbon group having 1 to 30 carbon atoms and at least one fluorine atom.

15. The fluoropolymer composite material of claim 14, wherein all hydrogen atoms of $R^4$ are substituted by fluorine atoms.

16. The fluoropolymer composite material of claim 15, wherein $R^4$ contains 4 to 12 carbon atoms.

17. The fluoropolymer composite material of claim 15, wherein $R^4$ contains 6 to 10 carbon atoms.

18. The fluoropolymer composite material of claim 1, wherein the fluoropolymer is a homopolymer, copolymer, terpolymer, or higher multipolymer comprising a recurring unit according to the formula

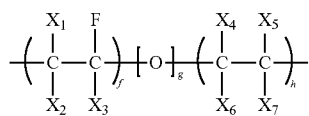

(5)

wherein $X_1$, $X_2$, $X_3$, $X_4$, $X_5$, $X_6$, and $X_7$ can be, independently within a unit and between units, a hydrogen atom, a fluorine atom, chorine atom, a group R representing a hydrocarbon group containing 1 to 6 carbon atoms or a fluoro-substituted hydrocarbon group containing 1 to 6 carbon atoms and at least one fluorine atom, or a group —OR;

the subscript f is a positive integer;

the subscript g is 0 or 1, where a value of 0 for a subscript represents the absence of a group to which the subscript is appended, and a value of 1 represents the presence of a group to which the subscript is appended; and the subscript h is 0 or a positive integer.

19. The fluoropolymer composite of claim 18, wherein the fluoropolymer is fluorinated ethylene propylene, polytetrafluoroethylene, a poly(perfluoroalkylvinylether), polyhexafluoropropylene, polyhexafluoropropylene oxide, polychlorotrifluoroethylene, polyvinylidene fluoride, polyvinylfluoride, poly(ethylene-tetrafluoroethylene), poly(ethylene-chlorotrifluoroethylene), or a copolymer, mixture, or combination thereof.

20. The fluoropolymer composite material of claim 1, further comprising crosslinked bonds.

21. The fluoropolymer composite material of claim 20, wherein the crosslinked bonds are between the fluoropolymer and particulate, or between fluoropolymer regions, or between particulates, or a combination thereof.

22. The fluoropolymer composite material of claim 20, wherein the crosslinked bonds comprise linked vinyl groups, ester linkages, amido linkages, ether linkages, urea linkages, carbamate linkages, imido linkages, diazene linkages, or a combination thereof.

23. The fluoropolymer composite material of claim 20, wherein the crosslinked bonds comprise linked vinyl groups.

24. A fluoropolymer composite material comprising a fluoropolymer having incorporated therein a carbon-based particulate having adhered to its surface an ionic compound of the general formula

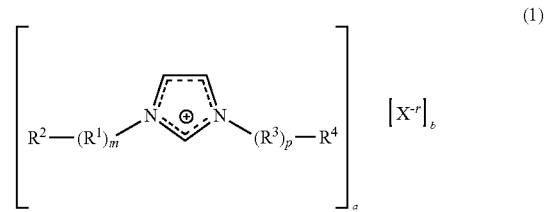

(1)

wherein:

$R^1$ and $R^3$ are, independently, hydrocarbon linking groups having at least one carbon atom, and optionally including one or more non-fluoro heteroatoms or heteroatom-containing groups;

$R^2$ is either a hydrogen atom, or a fluoro-substituted hydrocarbon group having at least one carbon atom and at least one fluorine atom and optionally including one or more non-fluoro heteroatoms or heteroatom-containing groups, or a heteroatom-containing group only when m is 1, wherein —$R^1$—$R^2$ represents a vinyl group;

$R^4$ is a fluoro-substituted hydrocarbon group having at least one carbon atom and at least one fluorine atom and optionally including one or more non-fluoro heteroatoms or heteroatom-containing groups;

the subscripts m and p are independently 0 or 1, where a value of 0 for a subscript represents the absence of a group to which the subscript is appended, and a value of 1 represents the presence of a group to which the subscript is appended;

$X^{-r}$ represents an anion with negative charge –r, where r is a value of 1, 2, or 3; and the subscripts a and b are positive integers such that a=b×r.

25. A fluoropolymer composite material comprising a fluoropolymer having incorporated therein a carbon-based particulate having adhered to its surface an ionic compound of the general formula

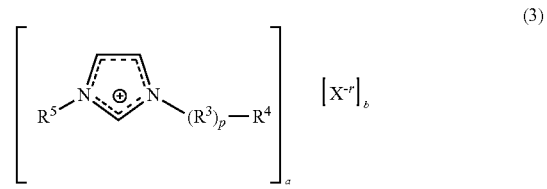

(3)

wherein:

$R^3$ is a hydrocarbon linking group having 1 to 6 carbon atoms;

$R^4$ is a fluoro-substituted hydrocarbon group having 1 to 30 carbon atoms and at least one fluorine atom;

$R^5$ is a hydrocarbon group having 1 to 6 carbon atoms;

the subscript p is 0 or 1, where a value of 0 for a subscript represents the absence of a group to which the subscript is appended, and a value of 1 represents the presence of a group to which the subscript is appended, wherein $R^5$ represents a vinyl group;

$X^{-r}$ represents an anion with negative charge $-r$, where r is a value of 1, 2, or 3; and the subscripts a and b are positive integers such that $a=b\times r$.

26. The fluoropolymer composite material of claim 25, wherein $R^4$ contains 4 to 12 carbon atoms and at least one fluorine atom.

27. The fluoropolymer composite material of claim 25, wherein $R^4$ contains 6 to 10 carbon atoms and at least one fluorine atom.

28. The fluoropolymer composite material of claim 25, wherein $R^5$ contains 1 to 3 carbon atoms.

* * * * *